US008513486B2

(12) United States Patent
Du et al.

(10) Patent No.: US 8,513,486 B2
(45) Date of Patent: Aug. 20, 2013

(54) CELL NUCLEAR TRANSFER

(75) Inventors: Yutao Du, Tjele (DK); Lars Axel Bolund, Skødstrup (DK); Gabor Vajta, Tjele (DK); Peter Michael Kragh, Risskov (DK)

(73) Assignee: Aarhus Universitet, Arhus C (DK)

( * ) Notice: Subject to any disclaimer, the term of this patent is extended or adjusted under 35 U.S.C. 154(b) by 400 days.

(21) Appl. No.: 12/066,169

(22) PCT Filed: Sep. 8, 2006

(86) PCT No.: PCT/DK2006/000498
§ 371 (c)(1),
(2), (4) Date: Dec. 30, 2008

(87) PCT Pub. No.: WO2007/028396
PCT Pub. Date: Mar. 15, 2007

(65) Prior Publication Data
US 2009/0119787 A1 May 7, 2009

(30) Foreign Application Priority Data

Sep. 8, 2005 (DK) .............................. 2005 01256
Mar. 3, 2006 (DK) .............................. 2006 00316
May 4, 2006 (DK) .............................. 2006 00626

(51) Int. Cl.
*C12N 15/00* (2006.01)
*C12N 15/02* (2006.01)

(52) U.S. Cl.
USPC ............. 800/24; 435/449; 435/440; 435/455

(58) Field of Classification Search
None
See application file for complete search history.

(56) References Cited

FOREIGN PATENT DOCUMENTS

| WO | WO98/29532 | 7/1998 |
| WO | WO00/30441 | 6/2000 |
| WO | WO01/00795 | 1/2001 |
| WO | WO01/96532 | 12/2001 |
| WO | WO02/086103 | 10/2002 |

OTHER PUBLICATIONS

Bondioli et al. (2001) Molec Reprod and Dev, vol. 60, pp. 189-195.*
Mereilles et al, Genomics, 2001, 158:351-356.*
Mitalipov Methods in Mol. Bio, 348: 151-168, (2006).*
Simerly et al. Science, 300:297 (2003).*
Vogel, Science, 300:225 and 227 (2003).*
Fehilly et al. Interspecific chimerism between sheep and Goat, Nature, 1984, vol. 307, pp. 634-636.*
Dobrinsky (2002) Theriogenology, 57:285-302.*
Nguyen (2000) Theriogenology, 56:1439-1448.*
Onisi et al, Science, 2000, 289:1188-1190.*
Booth et al. Application of the Zona-Free Manipulation Technique to Porcine Somatic Nuclear Transfer, Cloning and Stem Cells, vol. 3(4):191-197, 2001.
Booth et al. Simplification of bovine somatic cell nuclear transfer by application of a zona-free manipulation technique, Cloning and Stem Cells, vol. 3(3):139-150, 2001.
Du et al. High Overall in vitro Efficiency of Porcine Handmade Cloning Combining Partial Zona Digestion and Oocyte Trisection with Sequential Culture, Cloning and Stem Cells, vol. 7(3):199-204, 2005.
Kragh et al. Efficient in vitro production of porcine blastocysts by handmade cloning with a combined electrical and chemical activation, Theriogenology 64, 1536-1545, 2005.
Kragh et al. Production of transgenic porcine blastocysts by handmade cloning, Reproduction, Fertility and Development, 16, 315-318, 2004.
Oback et al. Cloned cattle derived from a novel zona-free embryo reconstruction system. Cloning and Stem Cells, vol. 5(1) 3-12, 2003.
Pedersen et al. Clinical experience with embryos produced by handmade cloning: work in progress. Molecular and Cellular Endocrinology 234, 137-143, 2005.
Peura et al. A comparison of established and new approaches in ovine and bovine nuclear transfer, Cloning and Stem Cells, vol. 5(4) 257-277, 2003.
Ritsuko et al. Cryoperservation of porcine embryos derived from in vitro-matured oocytes. Biology of Reproduction 71, 432-437, 2004.
Vajta et al. Hand-made cloning approach: potentials and limitations, Reproduction, Fertility and Development, 2005, 17, 1-6.
Vajta et al. Handmade somatic cell cloning in Cattle: Analysis of Factors Contributing to High Efficiency in Vitro, Biology of Reproduction, 68, 571-578, 2003.
Vajta et al. Production of a healthy calf by somatic cell nuclear transfer without micromanipulators and carbon dioxide incubators using the Hand-made Cloning (HMC), Theriogenology 62, 2004, 1465-1472.
Vajta et al. Science and Technology of farm animal cloning. State of the Art. Animal Reproduction Science 92, 2006, 211-230.
Vajta. Oocyte and embryo vitrification. Reproduction in Domestic Animals, vol. Suppl. 6, 2000, 45-48.
Andersen et al., (2002) Mechanisms underlying targeted gene correction using chimeric RNA DNA and single-stranded DNA oligonucleotides, J Mol Med 80:770-781.
Dobrinsky et al., (1996), Development of a Culture Medium (BECM-3) for Porcine Embryos: Effects of Bovine Serum Albumin and Fetal Bovine Serum on Embryo Development, Biol. Reprod. 55, 1069-1074.
Feltrin et al. (2006), Abstract, 35 In Vitro bovine embryo development after nuclear transfer by handmade cloning using a modified wow culture system, Reprod. Fertil. Dev. 18:126.
Hoshino et al. (2005), Developmental Competence of Somatic Cell Nuclear Transfer Embryos Reconstructed from Oocytes Matured In Vitro with Follicle Shells in Miniature Pig, Cloning and Stem Cells, vol. 7(1):17-26.
Hyttel et al., Vitrification of Bovine Oocytes With the Open Pulled Straw Method Ultrastructural Consequences, Molecular Reprod Dev 56:80-88, 2000.

(Continued)

*Primary Examiner* — Valarie Bertoglio
(74) *Attorney, Agent, or Firm* — Iver P. Cooper

(57) ABSTRACT

The present invention discloses methods for cell nuclear transfer that comprise for example modification of zona pellucida of an oocyte, and/or sectioning of oocytes into several parts. The present invention also discloses methods for producing a genetically modified non-human mammal. Genetically modified non-human mammals obtainable by the disclosed methods are also within the scope of the present invention. Disclosed are also methods for cryopreservation of cells.

35 Claims, 6 Drawing Sheets

(56) References Cited

OTHER PUBLICATIONS

Hyun et al., (2003), Production of Nuclear Transfer Derived Piglets Using Porcine Fetal Fibroblasts Transfected with the Enhanced Green Fluorescent Protein, Biology of Reproduction 69(3):1060-8.

Hyun et al., Effect of maturation media and oocytes derived from sows or gilts on the development of cloned pig embryos, Theriogenology 59 (2003) 1641-1649.

Ivics et al. (1997), Molecular Reconstruction of Sleeping Beauty, a Tc1-like Transposon from Fish, and Its Transposition in Human Cells, Cell, vol. 91, 501-510.

Kikuchi et al., (1999), Developmental Competence, after Transfer to Recipients, of Porcine Oocytes Matured, Fertilized, and Cultured In Vitro, Biology of Reproduction, 60(2):336-40.

Kikuchi et al., (2002), Successful Piglet Production after Transfer of Blastocysts Produced by a Modified In Vitro System, Biology of Reproduction 66, 1033-1041.

Liu et al., (2002), Targeted beta-globin gene conversion in human hematopoietic CD34+ and Lin-CD38-cells, Gene Ther. vol. 9(2):118-126.

Peura et al., The Effect of Recipient Oocyte Volume on Nuclear Transfer in Cattle, Molecular Reproduction and Development 50:185-191, 1998.

Reed et al., (Jan., 1992), In vitro culture of pig embryos, Theriogenology vol. 37(1):95-109.

Sørensen et al., (2005), Site-specific strand bias in gene correction using single-stranded oligonucleotides, J Mol Med 83:39-49.pdf.

Sørensen et al., (Ferbuary, 1999), Identification of Novel and Known Mutations in the Genes for Keratin 5 and 14 in Danish Patients with Epidermolysis Bullosa Simplex: Correlation Between Genotype and Phenotype, J Invest Dermatol., 112(2):184-90.

Tecirlioglu et al. Technical Report. Birth of a cloned calf derived from a vitrified hand-made cloned embryo. Reproduction, Fertility and Development, vol. 15, 2003, pp. 361-366.

Urnov et al., (Jun. 2005), Highly efficient endogenous human gene correction using designed zinc-finger nucleases, Nature vol. 435(2):646-651.

Walker et al., (2002), A Highly Efficient Method for Porcine Cloning by Nuclear Transfer Using In Vitro—Matured Occytes, Cloning and Stem Cells vol. 4(2):105-110.

Wu et al., Birth of piglets by in vitro fertilization of zonafree porcine oocytes, Theriogenology 62, 1544-1556, 2004.

* cited by examiner

A

B

CELL NUCLEAR TRANSFER

FIELD OF INVENTION

The present invention relates to a method of cell nuclear transfer in mammals, and to genetically modified mammals obtained or genetically modified animals that can be obtained by the method. Furthermore the present invention relates to a method of vitrifying oocytes, zygotes, embryos including blastocysts.

BACKGROUND OF INVENTION

The ability to genetically modify donor cells and using them for nuclear transfer provides a tool for the production of genetically modified animals which may be used for example as disease models for the study of serious human diseases and drug testing.

Traditional cell nuclear transfer techniques involve two steps of micromanipulation. A first step involves the enucleation of a mature oocyte, and a second step encompasses the transfer of a donor nucleus. Micromanipulation, however, has proven to have several disadvantages for example the need for expensive equipment, the need for highly skilled personnel and time-consuming work.

An improved method of nuclear transfer employing somatic cells as donor cells has been developed recently, a method known as Hand-Made Cloning (HMC) which involves the use of zona pellucida free oocytes. The method is simplified in comparison with the traditional nuclear transfer as micromanipulation is no longer needed. The method has been used in bovine (Vajta et al. 2001 Cloning 3, 89-95; Vajta et al. 2003 Biol. Reprod. 68, 571-578; Vajta et al. 2005 Reprod, Fertil. Dev. 17, 1-16; Tecirlioglu, et al., 2004). Also the use of zona-free nuclear transfer with one step of micromanipulation has been described for bovine (Booth et al. 2001 Cloning Stem Cells 3, 139-150; Oback et al. Cloning Stem Cells 5, 3-12) and porcine (Booth et al. 2001 Cloning Stem Cells 3, 191-197). The fact that this method is technically less demanding and less time-consuming has prompted researchers to suggest applying the HMC technique to other species. However, a number of technical problems made HMC application in pig more demanding than originally supposed. One of the problems encountered relates to low buoyant densities of porcine oocytes, both Zona intact (ZI) and especially zona-free (ZF) porcine oocytes. Consequently, porcine oocytes do not settle to the bottom of the dish. Furthermore, the surface of the oocytes is sticky and it is hard to avoid their attachment to each other when zona is removed. Moreover, ZF porcine oocytes are very fragile and it is difficult to bisect them in the way as described for bovine oocytes.

Recently, the HMC technique was, however with low efficiency, applied in porcine nuclear transfer, using genetically modified somatic cells, fibroblasts, as donor cells resulting in the production of genetically modified cloned blastocysts (Kragh et al. 2004 Reproduction, Fertility and Development 16, 315-318).

The present invention improves the technique for somatic cell nuclear transfer through HMC resulting in an increased embryo reconstruction rate and consequently the chance of obtaining genetically modified animals is increased significantly.

An obstacle to producing genetically modified animals by nuclear transfer methods at a large scale is the inability of cryopreserving pig oocytes and embryos using methods applied to other species. This is due to a high lipid content of porcine oocytes and embryos. Cryopreservation of cloned porcine embryos may considerably improve the output of somatic cell cloning by alleviating logistic problems. However, recently a noninvasive procedure was published for delipation of porcine embryos with centrifugation but without subsequent micromanipulation (Esaki et al. 2004 Biol Reprod. 71, 432-6).

SUMMARY OF INVENTION

The present invention relates in one aspect to a method of cell nuclear transfer comprising the steps of a) establishing at least one oocyte having at least a part of a modified zona pellucida, b) separating the oocyte into at least two parts obtaining at least one cytoplast, c) establishing a donor cell or cell nucleus having desired genetic properties, d) fusing at least one cytoplast with the donor cell or membrane surrounded cell nucleus, e) obtaining a reconstructed embryo.

A second aspect of the invention relates to a method of cell nuclear transfer comprising the steps of a) establishing at least one oocyte, b) separating the oocyte into at least three parts obtaining at least two cytoplasts, c) establishing a donor cell or cell nucleus having desired genetic properties, d) fusing at least one cytoplast with the donor cell or membrane surrounded cell nucleus, e) obtaining a reconstructed embryo.

A third aspect of the invention concerns a method for producing a genetically modified or transgenic non-human mammal comprising the steps of a) establishing at least one oocyte having at least a part of a modified zona pellucida, b) separating the oocyte into at least two parts obtaining an oocyte having a nucleus and at least one cytoplast, c) establishing a donor cell or cell nucleus with desired genetic properties, d) fusing at least one cytoplast with the donor cell or membrane surrounded cell nucleus, e) obtaining a reconstructed embryo, f) activating the reconstructed embryo to form an embryo, g) culturing said embryo, and h) transferring said cultured embryo to a host mammal such that the embryo develops into a genetically modified fetus.

A fourth aspect of the invention relates to a method for producing a genetically engineered or transgenic non-human mammal comprising the steps of a) establishing at least one oocyte, b) separating the oocyte into at least three parts obtaining at least one cytoplast, c) establishing a donor cell or cell nucleus having desired genetic properties, d) fusing at least one cytoplast with the donor cell or membrane surrounded cell nucleus, e) obtaining a reconstructed embryo, f) activating the reconstructed embryo to form an embryo, g) culturing said embryo, and h) transferring said cultured embryo to a host mammal such that the embryo develops into a genetically modified fetus.

In a fifth aspect the present invention relates to a method for cryopreservation of a pig embryo comprising the steps of a) establishing at least one pig oocyte, b) delipating the oocyte, c) activating the reconstructed embryo to form an embryo, d) culturing said embryo, e) vitrifying the embryo.

In a sixth aspect the invention relates to a method for cloning a non-human mammal comprising the steps of a) establishing an embryo as obtained by procedures according to the present invention, optionally thawing an embryo, b) transferring said cultured embryo to a host mammal such that the embryo develops into a genetically modified fetus.

In an seventh aspect the invention relates to a genetically modified non-human mammal obtainable by the method as defined herein.

In yet another aspect the invention relates to a genetically modified non-human embryo obtainable by the method as defined herein.

In yet a further aspect the invention relates to a genetically modified non-human embryo obtainable by the method as defined herein, having in its tissue cells mitochondria from at least three different maternal sources.

In a final aspect the invention relates to a method of culturing a reconstructed embryo (embryo) comprising the steps of a) establishing at least one oocyte having at least a part of zona pellucida, b) separating the oocyte into at least two parts obtaining an oocyte having a nucleus and at least one cytoplast, c) establishing a donor cell or cell nucleus having desired genetic properties, d) fusing at least one cytoplast with the donor cell or membrane surrounded cell nucleus, e) obtaining the reconstructed embryo, f) activating the reconstructed embryo to form an embryo, and e) culturing said embryo

DETAILED DESCRIPTION OF THE INVENTION

Figure 1:
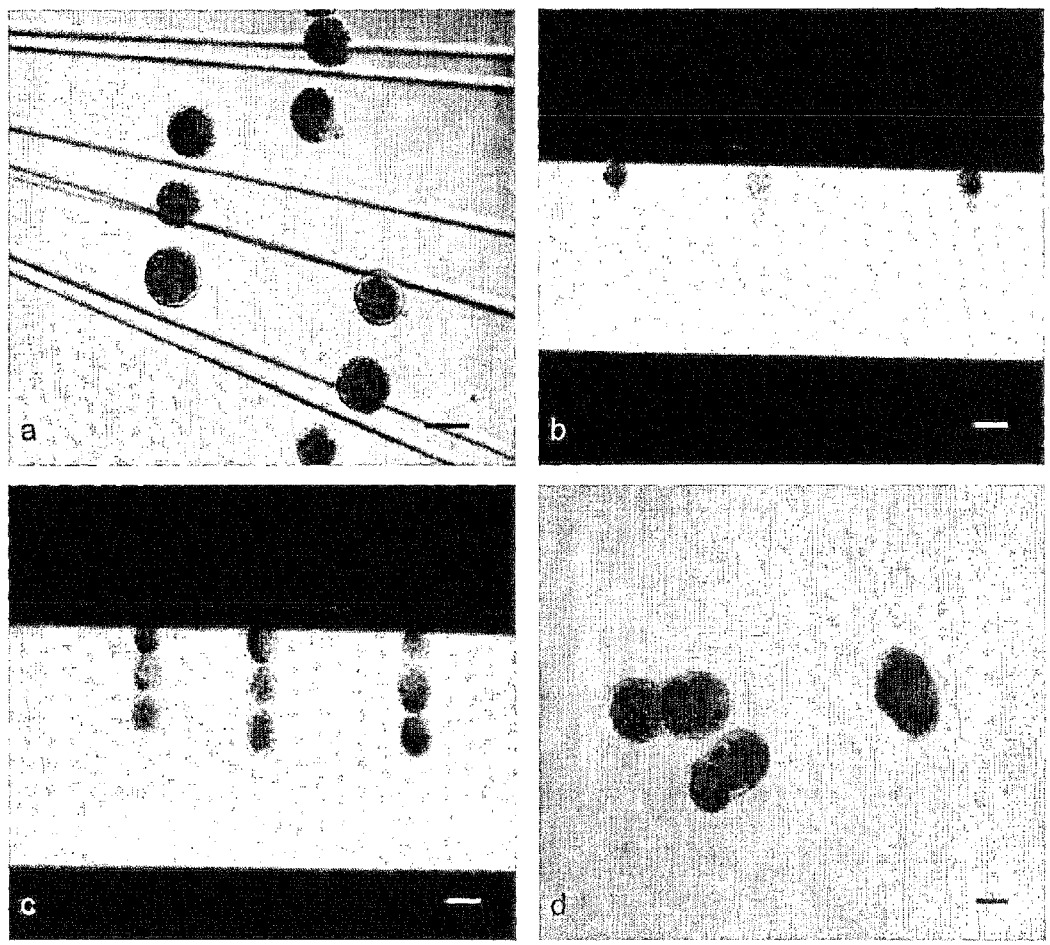
FIG. 1. (a) Oocytes trisection; (b) couplets of fibroblast-oocyte fragment for the first fusion; (c) embryos reconstructed with triplets (note elongation under the AC currency); (d) triplets fusion. Scale bar=50 m.

The present invention provides improved procedures for cloning mammals by nuclear transfer which refers to introducing a full complement of nuclear DNA from one cell to an enucleated cell.

Somatic Cell Nuclear Transfer

In cloning, the transfer of the nucleus of a somatic (body) cell or somatic cell into an egg cell (oocyte) which has had its own nucleus removed (denucleated or enucleated) is called somatic cell nuclear transfer. The new individual will develop from this reconstructed embryo and be genetically identical to the donor of the somatic cell. In the present invention the method of somatic cell nuclear transfer is a method of cell nuclear transfer comprising the steps of a) establishing at least one oocyte having at least a part of a modified zona pellucida, b) separating the oocyte into at least two parts obtaining at least one cytoplast, c) establishing a donor cell or cell nucleus having desired genetic properties, d) fusing at least one cytoplast with the donor cell or membrane surrounded cell nucleus, e) obtaining a reconstructed embryo. However, the present invention also relates to a method of cell nuclear transfer comprising the steps of a) establishing at least one oocyte, b) separating the oocyte into at least three parts obtaining at least two cytoplasts, c) establishing a donor cell or cell nucleus having desired genetic properties, d) fusing at least one cytoplast with the donor cell or membrane surrounded cell nucleus, e) obtaining a reconstructed embryo.

The parameters for the listed steps can be varied in order to obtain the most efficient nuclear transfer for a given animal species. The various parameters are described in detail below.

Oocyte

The term 'oocyte' according to the present invention means an immature female reproductive cell, one that has not completed the maturing process to form an ovum (gamete). In the present invention an enucleated oocyte is the recipient cell in the nuclear transfer process.

The oocytes according to the present invention are isolated from oviducts and/or ovaries of a mammal. Normally, oocytes are retrieved from deceased animals, although they may be isolated also from either oviducts and/or ovaries of live animals. In one embodiment the oocytes are isolated by oviductal recovery procedures or transvaginal recovery methods. In a preferred embodiment the oocytes are isolated by aspiration. Oocytes are typically matured in a variety of media known to a person skilled in the art prior to enucleation. The oocytes can also be isolated from the ovaries of a recently sacrificed animal or when the ovary has been frozen and/or thawed. Preferably, the oocytes are freshly isolated from the oviducts.

Oocytes or cytoplasts may also be cryopreserved before use. While it will be appreciated by those skilled in the art that freshly isolated and matured oocytes are preferred, it will also be appreciated that it is possible to cryopreserve the oocytes after harvesting or after maturation. If cryopreserved oocytes are utilised then these must be initially thawed before placing the oocytes in maturation medium. Methods of thawing cryopreserved materials such that they are active after the thawing process are well-known to those of ordinary skill in the art. However, in general, cryopreservation of oocytes and cytoplasts is a very demanding procedure, and it is especially difficult in pigs, because of the above mentioned general fragility of pig oocytes and cytoplasts, and because of the high lipid content that makes them very sensitive to chilling injury (i.e. injury that occurs between +15 and +5° C. during the cooling and warming procedure).

In another embodiment, mature (metaphase II) oocytes that have been matured in vivo, may be harvested and used in the nuclear transfer methods disclosed herein.

Essentially, mature metaphase II oocytes are collected surgically from either nonsuperovulated or superovulated mammals 35 to 48 hours past the onset of estrus or past the injection of human chorionic gonadotropin (hCG) or similar hormone.

Where oocytes have been cultured in vitro, cumulus cells that are surrounding the oocytes in vivo may have accumulated may be removed to provide oocytes that are at a more suitable stage of maturation for enucleation. Cumulus cells may be removed by pipetting or vortexing, for example, in the presence of in the range of 0.1 to 5% hyaluronidase, such as in the range of 0.2 to 5% hyaluronidase, for example in the range of 0.5 to 5% hyaluronidase, such as in the range of 0.2 to 3% hyaluronidase, for example in the range of 0.5 to 3% hyaluronidase, such as in the range of 0.5 to 2% hyaluronidase, for example in the range of 0.5 to 1% hyaluronidase, such as 0.5% hyaluronidase.

The first step in the preferred methods involves the isolation of a recipient oocyte from a suitable animal. In this regard, the oocyte may be obtained from any animal source and at any stage of maturation.

The stage of maturation of the oocyte at enucleation and nuclear transfer has been reported to be of significance for the success of nuclear transfer methods. Immature (prophase I) oocytes from mammalian ovaries are often harvested by aspiration. In order to employ techniques such as genetic engineering, nuclear transfer and cloning, such harvested oocytes are preferably matured in vitro before the oocyte cells may be used as recipient cells for nuclear transfer.

Preferably, successful mammalian embryo cloning uses the metaphase II stage oocyte as the recipient oocyte because it is believed that at this stage of maturation the oocyte can be or is sufficiently activated to treat the introduced nucleus as if it were a fertilising sperm. However, the present invention relates to any maturation stage of the oocyte which is suitable for carrying out somatic cell nuclear transfer, embryos, blastocysts, and/or animals obtainable by the method of somatic cell nuclear transfer of the present invention.

The in vitro maturation of oocytes usually takes place in a maturation medium until the oocyte has reached the metaphase II stage or has extruded the first polar body. The time it takes for an immature oocyte to reach maturation is called the maturation period.

In a preferred embodiment of the present invention the oocyte is from sow or gilt, preferably from a sow.

Animals

The donor (somatic cell or nucleus of somatic cell) and recipient (cytoplast) involved in the cell nuclear transfer method according to the present invention is a non-human mammal. Likewise, the animal in which reconstructed embryos may be implanted in according to the present invention is a non-human mammal. The mammal may be an ungulate selected from the group consisting of domestic or wild representatives of bovidae, ovids, cervids, suids, equids and camelids. In a particular embodiment the mammal is a cow or bull, bison, buffalo, sheep, big-horn sheep, horse, pony, donkey, mule, deer, elk, caribou, goat, water buffalo, camel, llama, alpaca or pig.

In a special embodiment of the present invention the mammal is a pig. In one embodiment the pig is a wild pig. In another embodiment the pig is the domestic pig *Sus scrofa*, or *S. domesticus*. In yet another embodiment the invention relates to mini pig, but also to inbred pigs.

In a specific embodiment the pig may be selected from the group consisting of Landrace, Yorkshire, Hampshire, Duroc, Chinese Meishan, Berkshire and Piêtrain. In yet another embodiment the present invention relates to the group consisting of Landrace, Yorkshire, Hampshire and Duroc. However the present invention also relates to the group consisting of Landrace, Duroc and Chinese Meishan. Similarly, the group consisting of Berkshire, Pietrain, Landrace and Chinese Meishan can be objects of the present invention. But also the group consisting of Landrace and Chinese Meishan are objects of the present invention.

In a particular embodiment the pig is a Landrace pig, or a Yorkshire pig. In a particular embodiment the invention relates to pigs of the breed Hampshire, but also Duroc. In yet another preferred embodiment the pig is of the breed Chinese Meishan. However, also Berkshire is covered by the invention, and in a special embodiment Piêtrain is covered by the present invention.

Another embodiment of the present invention relates to mini pigs selected from the group consisting of Goettingen, Yucatan, Bama Xiang Zhu, Wuzhishan, Xi Shuang Banna.

In other embodiments the invention relates to the group consisting of Goettingen, Yucatan. Alternatively, the invention relates to the group consisting of Bama Xiang Zhu, Wuzhishan, Xi Shuang Banna. In particular the invention relates to Goettingen. But also Yucatan is relevant for the invention. Similarly, Bama Xiang Zhu is covered by the invention, also Wuzhishan, and in particular Xi Shuang Banna.

The donor mammals according to the present invention may be female, or male. The age of the mammal can be any age such as an adult, or for example a fetus.

Embryo

According to the present invention a reconstructed embryo (i.e. single cell embryo) contains the genetic material of the donor cell. Subsequently, the reconstructed embryo divides progressively into a multi-cell embryo after the onset of mitosis. In vitro the onset of mitosis is typically induced by activation as described herein.

In the present invention the term 'embryo' also refers to reconstructed embryos which are embryos formed after the process of nuclear transfer after the onset of mitosis by activation. Reconstructed embryos are cultured in vitro.

When the embryo contains about 12-16 cells, it is called a "morula". Subsequently, the embryo divides further and many cells are formed, and a fluid-filled cystic cavity within its center, blastocoele cavity. At this stage, the embryo is called a "blastocyst". The developmental stage of the "fertilized" oocyte at the time it is ready to implant; formed from the morula and consists of an inner cell mass, an internal cavity, and an outer layer of cells called trophectodermal cells.

The blastocyst according to the present invention may be implanted into the uterus of a host mammal and continues to grow into a fetus and then an animal.

In the methods provided herein for producing genetically modified or transgenic non-human mammal, for cloning a non-human mammal, for culturing a reconstructed embryo, and/or for cryopreservation of a pig embryo, the embryo may be cultured in vitro. The embryo may for example be cultured in sequential culture. It will be appreciated that the embryo may be a normal embryo, or a reconstructed embryo as defined elsewhere herein.

Cytoplast

An oocyte or a part of an oocyte from which the nucleus has been removed.

Donor Cell

By the term 'donor cell' of the present invention is meant somatic cell and/or cells derived from the germ line.

By the term 'somatic cell' of the present invention is meant any (body) cell from an animal at any stage of development. For example somatic cells may originate from fetal or adult tissue. Especially preferred somatic cells are those of foetal origin. However, cells from a germ line may also be used. According to the present invention a donor cell is a somatic cell. In another embodiment of the present invention the donor cell is a cell derived from a germ cell line.

In a preferred embodiment of the present invention the donor cell harbours desired genetic properties. However, the donor cell may harbour desired genetic properties which have been gained by genetic manipulation as described elsewhere herein.

Somatic cells are selected from the group consisting of epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells.

These may be obtained from different organs, e.g., skin, lung, pancreas, liver, stomach, intestine, heart, reproductive organs, bladder, kidney, urethra and other urinary organs.

The animals from which the somatic cells may be derived are described elsewhere herein. A preferred embodiment of the invention is the use of somatic cells originating from the same species as the recipient oocyte (cytoplast).

Preferably, the somatic cells are fibroblast cells as the can be obtained from both developing fetuses and adult animals in large quantities. Fibroblasts may furthermore be easily propagated in vitro. Most preferably, the somatic cells are in vitro cultured fibroblasts of foetal origin.

In a preferred embodiment the somatic cells are genetically modified. In yet a further preferred embodiment of the present invention the somatic cells are pig cells, and preferably of foetal origin, or for example from adults.

Enucleation

The method of enucleation of an oocyte may be selected from the group of methods consisting of aspiration, physical removal, use of DNA-specific fluorochromes, exposure to ultraviolet light and/or chemically assisted enucleation. In one embodiment the present invention relates to the use of DNA-specific fluorochromes.

Enucleation may, however, be performed by exposure with ultraviolet light. In a particular embodiment enucleation is chemically assisted prior to physical removal of the nucleus. Chemically assisted enucleation using for example antineoplastic agents, such as demecolcine (N-deacetyl-N-methyl 1 colchicine), and/or for example etoposide or related agents may be performed prior to enzymatic modification of zona pellucida. Chemically assisted enucleation comprises culturing matured COCs in maturation medium as described elsewhere herein supplemented with demecolcine for a particular period of time. In the range of 0.1 µg/ml to 10 µg/ml demecolcine, such as 0.2 µg/ml to 10 µg/ml, for example 0.3 µg/ml to 10 µg/ml, such as 0.25 µg/ml to 5 µg/ml, for example 0.3 µg/ml to 1 µg/ml, such as 0.25 µg/ml to 0.5 µg/ml, for example 0.4 µg/ml demecolcin may be supplemented to the maturation medium. Similarly, maturation medium may be supplemented with etoposide for example in the range of 0.1 µg/ml to 10 µg/ml etoposide, such as 0.2 µg/ml to 10 µg/ml, for example 0.3 µg/ml to 10 µg/ml, such as 0.25 µg/ml to 5 µg/ml, for example 0.3 µg/ml to 1 µg/ml, such as 0.25 µg/ml to 0.5 µg/ml, for example 0.4 µg/ml etoposide may be supplemented to the maturation medium. The time for culturing the COCs in the presence of antineoplastic agents ranges from 10 min to 5 hrs, such as 30 minutes to 5 hrs, for example 10 minutes to 2 hrs, such as 30 min to 2 hrs, for example 10 min to 1.5 hrs, such as 20 min to 3 hrs, for example 10 min to 3 hrs, such as 30 min to 1.5 hrs, for example 45 min.

In a particular embodiment chemically assisted enucleation is performed using 0.45 µg/ml demecolcine and/or etoposide added to the maturation medium for 45 min.

In a particular embodiment it is preferred that the enucleation is by physical removal of the nucleus. The physical removal may be by separation for example by bisection of the oocyte into two halves (two parts), one which contains the nucleus and the enucleated oocyte half, known as the cytoplast, removing the nucleated half of the oocyte and selecting the resulting cytoplast for further procedures of the invention. Alternatively the separation is by trisection, resulting in three parts of which two parts are cytoplasts. In another embodiment the oocyte may be separated into four parts, resulting in the production of three cytoplasts. The oocyte may even be separated into five parts by physical removal, resulting in four cytoplasts. Similarly, the oocyte may be separated into six parts, for example seven parts, such as eight parts, for example nine parts, such as ten or more parts.

The physical separation of the oocyte and subsequent removal of the nucleus-bearing part of the oocyte may be achieved by the use of a microsurgical blade.

The oocytes may be screened to identify which oocytes have been successfully enucleated. Oocyte parts that harbour nuclear DNA may be identified by staining with Hoechst fluorochrome, the staining procedure of which is known to a person skilled in the art. Oocyte parts harbouring nuclear DNA are discarded and the enucleated oocytes (cytoplasts) are selected for further procedures.

Zona Pellucida

Zona pellucida is a thick, transparent, noncellular layer or envelope of uniform thickness surrounding an oocyte Generally, an intact zona pellucida is considered to be important in cell nuclear transfer due to a number of parameters. One parameter is to keep the polar body close to the metaphase plate of the oocyte in order to indicate the appropriate site for enucleation. Another parameter relates to the keeping of the donor cell close to the oocyte cytoplast before and during fusion. The zona is also believed to confer protection for the donor cell and cytoplast during fusion. Finally, embryo development after reconstitution and activation is believed to be supported by the zona pellucida.

Modification of at least a part of the zona pellucida can be performed by a number of methods. For example physical manipulation can be used to modify the zona. But also chemical treatment with agents such as acidic solutions (acidic Tyrode) can be employed. One example of chemical agents that can be employed in the present invention is acidic solutions, for example Tyrode. In a particular embodiment of the invention the zona pellucida is modified by enzymatic digestion. Such enzymatic digestion may be performed by enzymes comprising for example trypsin. Alternatively a specific protease may be used, such as pronase.

In a preferred embodiment the enzymatic digestion results in at least a partial digestion of a part of zona pellucida which in a preferred embodiment of the present invention means that at least a part of the zona pellucida is being removed, or that the zona pellucida is partly removed. In the present context the zona pellucida is not completely removed.

According to an especially preferred embodiment of the present invention the partially digested part of zona pellucida is characterized by the zona pellucida still being visible and by the fact that the oocyte has not become misshaped.

The partial digestion may be achieved by exposure to a protease. In another embodiment of the present invention the partial digestion may be accomplished by the use of a pronase. In yet another embodiment the partial digestion may be achieved by a combination of a protease and pronase.

In a preferred embodiment the concentration of pronase is in the range of 0.1 mg/ml to 10 mg/ml, such as 0.5 mg/ml to 10 mg/ml, for example 1 mg/ml to 10 mg/ml, such as 1.5 mg/ml to 10 mg/ml, for example 2 mg/ml to 10 mg/ml, such as 2.5 mg/ml to 10 mg/ml, for example 2.75 mg/ml to 10 mg/ml, such as 3 mg/ml to 10 mg/ml, for example 3.25 mg/ml to 10 mg/ml, such as 3.3 mg/ml to 10 mg/ml, for example 3.5 mg/ml to 10 mg/ml.

A preferred embodiment is a pronase concentration in the range of 2 mg/ml to 5 mg/ml, such as 2.25 mg/ml to 5 mg/ml, for example 2.5 mg/ml to 5 mg/ml, such as 2.75 mg/ml to 5 mg/ml, for example 2.8 mg/ml to 5 mg/ml, such as 2.9 mg/ml to 5 mg/ml, for example 3 mg/ml to 5 mg/ml, such as 3.1 mg/ml to 5 mg/ml, for example 3.2 mg/ml to 5 mg/ml, such as 3.3 mg/ml to 5 mg/ml.

A particular embodiment of the present invention is a pronase concentration in the range of 1 mg/ml to 4 mg/ml, for example 1 mg/ml to 3.9 mg/ml, such as 1 mg/ml to 3.8 mg/ml, for example 1 mg/ml to 3.7 mg/ml, such as 1 mg/ml to 3.6 mg/ml, for example 1 mg/ml to 3.5 mg/ml such as 1 mg/ml to 3.4 mg/ml, for example 1 mg/ml to 3.3 mg/ml.

In a preferred embodiment the pronase concentration is in the range of 2.5 mg/ml to 3.5 mg/ml, such as 2.75 mg/ml to 3.5 mg/ml, for example 3 mg/ml to 3.5 mg/ml. In a special embodiment the pronase concentration is 3.3 mg/ml.

It is clear to the skilled person that the pronase should be dissolved in an appropriate medium, one preferred medium according to the present invention is T33 (Hepes buffered TCM 199 medium containing 33% cattle serum (as described earlier—Vajta, et al., 2003).

The time of incubation of the oocyte in the pronase solution is in the range of 1 second to 30 seconds, such as 2 seconds to 30 seconds, for example 3 seconds to 30 seconds, such as 4 seconds to 30 seconds, such as 5 seconds to 30 seconds.

In another embodiment of the present invention the incubation time is in the range of 2 seconds to 15 seconds, such as 2 seconds to 14 seconds, for example 2 seconds to 13 seconds, such as 2 seconds to 12 seconds, for example 2 seconds to 11 seconds, such as 2 seconds to 10 seconds, for example 2 seconds to 9 seconds, such as 2 seconds to 8 seconds, for example 2 seconds to 7 seconds, such as 2 seconds to 6 seconds, for example 2 seconds to 5 seconds.

In a particular embodiment of the present invention the incubation time is in the range of 3 seconds to 10 seconds, such as 3 seconds to 9 seconds, for example 4 seconds to 10 seconds, such as 3 seconds to 8 seconds, for example 4 seconds to 9 seconds, such as 3 seconds to 7 seconds, for example 4 seconds to 8 seconds, such as 3 seconds to 6 seconds, for example 4 seconds to 7 seconds, such as 3 seconds to 5 seconds, for example 4 seconds to 6 seconds, such as 4 seconds to 5 seconds. An especially preferred incubation time is 5 seconds.

In a preferred embodiment of the present invention the oocyte is treated for 5 seconds in a 3.3 mg/ml pronase solution at 39° C.

Reconstructed Embryo

By the term 'reconstructed embryo' is meant the cell which is formed by insertion of the donor cell or nucleus of the donor cell into the enucleated oocyte which corresponds to a zygote (during normal fertilisation). However, the term 'reconstructed embryo' is also referred to as the 'reconstituted cell'. In the present invention the donor cell is a somatic cell. However, the donor cell may also be derived from a germ line cell.

Fusion

The transfer of a donor cell or a membrane surrounded nucleus from a donor cell to at least cytoplast is according to the present invention performed by fusion. In the scenarios described below the term 'donor cell' also refers to a membrane surrounded nucleus from a donor cell. Fusion may be achieved by a number of methods.

Fusion may be between a donor cell and at least one cytoplast, such as between a donor cell and at least two cytoplasts, for example between a donor cell and at least two cytoplasts, such as between a donor cell and at least three cytoplasts, such as between a donor cell and at least four cytoplasts, for example between a donor cell and at least five cytoplasts, such as between a donor cell and at least six cytoplasts, for example between a donor cell and at least seven cytoplasts, such as between a donor cell and at least eight cytoplasts.

Fusion may be performed according to the listed combinations above simultaneously or sequentially. In one embodiment of the present invention the fusion is performed simultaneously. In another embodiment fusion of the at least one cytoplast and a donor cell is performed sequentially.

For example fusion may be achieved by chemical fusion, wherein a donor cell and the at least one cytoplast are exposed to fusion promoting agents such as for example proteins, glycoproteins, or carbohydrates, or a combination thereof. A variety of fusion-promoting agents are known for example, polyethylene glycol (PEG), trypsin, dimethylsulfoxide (DMSO), lectins, agglutinin, viruses, and Sendai virus. Preferably phytohemaglutinin (PHA) is used. However mannitol and, or polyvinylalcohol may be used.

Alternatively, fusion may be accomplished by induction with a direct current (DC) across the fusion plane. Often an alternating current (AC) is employed to align the donor and recipient cell. Electrofusion produces a sufficiently high pulse of electricity which is transiently able to break down the membranes of the cytoplast and the donor cell and to reform the membranes subsequently. As a result small channels will open between the donor cell and the recipient cell. In cases where the membranes of the donor cell and the recipient cell connect the small channels will gradually increase and eventually the two cells will fuse to one cell.

Alignment of the at least one cytoplast and the donor cell may be performed using alternating current in the range of 0.06 to 0.5 KV/cm, such as 0.1 to 0.4 KV/cm, for example 0.15 to 0.3 KV/cm. In a preferred embodiment alignment of the at least one cytoplast and the donor cell may be performed using alternating current at 0.2 KV/cm.

Fusion may be induced by the application of direct current across the fusion plane of the at least one cytoplast and the donor cell. Direct current in the range of 0.5 to 5 KV/cm, such as 0.75 to 5 KV/cm, for example 1 to 5 KV/cm, such as 1.5 to 5 KV/cm, for example 2 to 5 KV/cm. Another preferred embodiment of the present invention is the application of direct current in the range of 0.5 to 2 KV/cm. In a further preferred embodiment the direct current may be 2 KV/cm.

The direct current may preferably be applied for in the range of 1-15 micro seconds, such as 5 to 15 micro seconds, for example 5 to 10 micro seconds. A particular embodiment may be 9 micro seconds.

In an especially preferred embodiment fusion with direct current may be using a direct current of 2 KV/cm for 9 micro seconds.

Electrofusion and chemical fusion may however be also be combined.

Typically electrofusion is performed in fusion chambers as known to the skilled person.

Fusion may be performed in at least one step, such as in two steps, for example three steps, such as in four steps, for example in five steps, such as six steps, for example seven steps, such as in eight steps.

Fusion may be performed in for example a first step wherein the at least one cytoplast is fused to the donor cell. A second step of fusion may comprise fusion of the fused pair (cytoplast-donor cell, reconstructed embryo) with at least one cytoplast, such as at least two cytoplasts, for example three cytoplasts, such as four cytoplasts, for example five cytoplasts, such as six cytoplasts, for example seven cytoplasts, such as eight cytoplasts. The second step of fusion with fusion of at least one cytoplast and the fused pair may be performed sequentially or simultaneously. In one embodiment the at least two cytoplasts are fused to the fused pair simultaneously. In another embodiment the at least two cytoplasts are fused to the fused pair sequentially.

In one embodiment of the invention the second step of fusion may also be an activation step wherein the reconstructed embryo is activated to enter mitosis. As described elsewhere herein.

Activation

In a preferred embodiment the reconstructed embryo may be allowed to rest prior to activation for a period of time in order to allow for the nucleus of the donor cell to reset its genome and gain toti potency in the novel surroundings of the enucleated cytoplast. The reconstructed embryo may for example rest for one hour prior to activation.

Preferably, the reconstructed embryo may be activated in order to induce mitosis. Methods for activation may preferably be selected from the group of consisting of electric pulse, chemically induced shock, increasing intracellular levels of divalent cations or reducing phosphorylation. A combination of methods may be preferred for activation.

In one particular embodiment of the invention the activation and the second step of fusion may be performed simultaneously. However, the activation of the reconstituted embryo and the at least one additional step of fusion between the reconstructed embryo and the at least one cytoplast may be performed sequentially.

Reducing the phosphorylation of cellular proteins in the reconstructed embryo by known methods such as for example by the addition of kinase inhibitors may activate the reconstituted embryo. A preferred embodiment may involve the use of agents that inhibit protein synthesis, for example cycloheximide. A further preferred embodiment may be using agents that inhibit spindle body formation, for example cytochalasin B.

In one embodiment of the invention the intracellular levels of divalent cations may be increased. Divalent cations such as for example calcium may be in comprised in the activation medium. Preferably, the cations may enter the reconstructed embryo, particularly upon subjecting the reconstructed embryo to an electric pulse. In a preferred embodiment the electric pulse may cause entering of calcium into the reconstructed embryo.

The application of an electrical pulse using direct current may be an activation step. However, in a preferred embodiment the electrical pulse applied for activation may also serve as an additional fusion step.

Prior to applying an electrical pulse using direct current the at least one cytoplast and the at least one reconstructed embryo may be aligned by the application of alternating current. The alternating current may be in the range of the range of 0.06 to 0.5 KV/cm, such as 0.1 to 0.4 KV/cm, for example 0.15 to 0.3 KV/cm. In a preferred embodiment alignment of the at least one cytoplast and the donor cell may be performed using alternating current at 0.2 KV/cm.

Activation may be induced by the application of direct current across the fusion plane of the at least one cytoplast and the donor cell. Direct current in the range of 0.2 to 5 KV/cm, such as 0.4 to 5 KV/cm, for example 0.5 to 5 KV/cm. Another preferred embodiment of the present invention is the application of direct current in the range of 0.5 to 2 KV/cm. In a further preferred embodiment the direct current may be 0.7 KV/cm.

The direct current may preferably be applied for in the range of 10 to 200 micro seconds, such as 25 to 150 micro seconds, for example 50 to 100 micro seconds. A particular embodiment may be 80 micro seconds.

In an especially preferred embodiment fusion with direct current may be using a direct current of 0.7 KV/cm for 80 micro seconds.

An especially preferred embodiment of activation according to the present invention may be use of an electrical pulse in combination with subjecting the reconstructed embryo to agents that inhibit protein synthesis, spindle body formation, and divalent cations.

Activation may be performed by any combination of the methods described above.

Type of Genetic Modification

The donor cells may be genetically modified by any of standard method known in the art. The genetic modification may be a modification of the genomic DNA by deletion, insertion, duplication and/or other forms of mutation, including point mutation. The modification may be made in coding sequences and/or non-coding sequences. DNA constructs for insertion may harbour a gene of interest and/or regulatory sequences such as promoters, insulators, enhancers, repressors or ribosomal entry sites. In some embodiments, only one genetic modification is introduced in the genome. In other embodiments, however, the genome may be modified at more than one site. Suitable techniques for genetic modification of mammalian cells, such as fibroblasts, include techniques such as gene addition by nonhomologous recombination, gene replacement by homologous recombination, and gene editing. This may include the use of retroviral insertion, transposon transfer and/or artificial chromosome techniques. Non-homologous DNA recombination may e.g. be carried out as described in Kragh et al. (2004) Reprod. Fert. Dev. 16:290 or Kragh et al. (2004) Reprod. Fert. Dev. 16:315, Transposon-based gene transfer may be carried out as described in Izsvak et al. (1997) Cell 91:501. Gene replacement by homologous recombination may e.g. involve the techniques described by Urnow et al. (2005) Nature 435:646. Techniques for gene editing have been described in Andersen et al. (2002) J. Mol. Med. 80:770, Liu et al (2002) Gene Ther. 9:118 and Sørensen et al. (2005) J. Mol. Med. 83:39.

In Vitro Culture of Embryos

One aspect of the invention relates to a method of in vitro culturing embryos, whereby the blastocyst rate increased to 25.3%. Thus, a method of culturing a reconstructed embryo is within the scope of the present invention, comprising the steps of a) establishing at least one oocyte having at least a part of zona pellucida, b) separating the oocyte into at least two parts obtaining an oocyte having a nucleus and at least one cytoplast, c) establishing a donor cell or cell nucleus having desired genetic properties, d) fusing at least one cytoplast with the donor cell or membrane surrounded cell nucleus, e) obtaining the reconstructed embryo, f) activating the reconstructed embryo to form an embryo, and e) culturing said embryo.

Another aspect of the invention relates to a method of cell nuclear transfer in which a step of culturing the embryo is included.

In a preferred embodiment in relation to the methods described herein embryos are cultured in a sequential set of media. Preferably the blastocysts are grown in traditional medium such as for example NCSU37 or equivalent medium as known to a person skilled in the art, wherein glucose is removed and substituted by other agents. One agent may be pyruvate. Another agent may be lactate. The agents may also be combined and replace glucose in the traditional medium.

The embryos may be cultured in the substituted media as described above from Day 0 to Day 3, such as from Day 0 to Day 2.

The pyruvate concentration may range from 0.05 to 1 mM, such as 0.1 to 1 mM, for example 0.125 to 1 mM, such as 0.15 to 1 mM. However the concentration of sodium pyruvate may also range from 0.05 mM to 0.9 mM, such as 0.05 to 0.8 mM, for example 0.05 to 0.7 mM, such as 0.05 to 0.6 mM, for example 0.05 to 0.5 mM, such as 0.05 to 0.4 mM, for example 0.05 to 0.3 mM, such as 0.05 to 0.2 mM. Preferably the concentration ranges between 0.05 to 0.17 mM. A preferred concentration of sodium pyruvate is 0.17 mM.

The lactate concentration may range from 0.5 to 10 mM, such as 0.75 to 10 mM, for example 1 to 10 mM, such as 1.5 to 10 mM, such as 1.75 to 10 mM, for example 2 to 10 mM, such as 2.5 to 10 mM. However the concentration of sodium lactate may also range from 0.5 mM to 9 mM, such as 0.5 to 8 mM, for example 0.5 to 7 mM, such as 0.5 to 6 mM, for example 0.5 to 5 mM, such as 0.5 to 4 mM, for example 0.5 to 03 mM. Preferably the concentration ranges between 1 to 5 mM, such as 2 to 4 mM, for example 2 to 3 mM. A preferred concentration of sodium lactate is 2.73 mM.

After the initial glucose-free incubation medium glucose is again replacing the pyruvate and lactate. The embryos may be cultured in the glucose containing medium from Day 4 to Day 3, preferably from Day 3 to Day 7. The glucose concentration may range from 1 to 10 mM, such as 2 to 10 mM, for example 3 to 10 mM, such as 4 to 10 mM, for example 5 to 10 mM. However, the glucose concentration may also range from 1 to 9 mM, such as 2 to 8 mM, for example 3 to 7 mM, such as 4-6 mM. A preferred concentration of glucose according to the present invention is 5.5 mM of glucose.

In yet another preferred embodiment the embryo is a pig embryo.

Genetically Modified Animals

According to one embodiment of the present invention, genetically modified or transgenic animals are provided having desired genotypes.

It will be appreciated that the invention does not comprise processes for modifying the genetic identity of animals which are likely to cause them suffering without any substantial medical benefit to man or animal, or animals resulting from such processes.

The present invention relates to methods of producing a genetically modified or transgenic non-human mammal comprising a) establishing at least one oocyte having at least a part of a modified zona pellucida, b) separating the oocyte into at least two parts obtaining an oocyte having a nucleus and at least one cytoplast, c) establishing a donor cell or cell nucleus with desired genetic properties, d) fusing at least one cytoplast with the donor cell or membrane surrounded cell nucleus, e) obtaining a reconstructed embryo, f) activating the reconstructed embryo to form an embryo, g) culturing said embryo; and h) transferring said cultured embryo to a host mammal such that the embryo develops into a genetically modified fetus.

However genetically engineered or transgenic non-human mammals may also be produced by a method comprising: a) establishing at least one oocyte, b) separating the oocyte into at least three parts obtaining an oocyte having a nucleus and at least one cytoplast, c) establishing a donor cell or cell nucleus with desired genetic properties, d) fusing at least one cytoplast with the donor cell or membrane surrounded cell nucleus, e) obtaining a reconstructed embryo, f) activating the reconstructed embryo to form an embryo, g) culturing said embryo; and h) transferring said cultured embryo to a host mammal such that the embryo develops into a genetically modified fetus.

Organ or Tissue Donation

In one embodiment, the animals of the invention may be used as a source for organ or tissue donation for humans or other animals, either animals of the same species or animal of other species. Transfer between species is usually termed xenotransplantation. Entire organs that may be transplanted include the heart, kidney, liver, pancreas or lung. Alternatively, parts of organs, such as specific organ tissues may be transplanted or transferred to humans or other animals. In a yet further embodiment, an individual cell or a population of individual cells from an animal of the invention may be transferred to a human being or another animal for therapeutic purposes.

Disease Models

The present invention also relates to a method for cloning a non-human mammal according to the methods of the present invention. Thus, one aspect of the invention concerns a method for cloning a non-human mammal comprising a) establishing a blastocyst as described herein, optionally thawing an embryo, b) transferring said cultured embryo to a host mammal such that the embryo develops into a genetically modified fetus. The genetically modified fetus may develop into a non-human mammal.

The present invention also covers genetically modified animal as disease models obtainable by the methods described herein. Therefore, a second aspect of the invention is a genetically modified non-human mammal obtainable by the methods described herein. Another aspect concerns a genetically modified non-human embryo. obtainable by the methods described herein.

The methods described herein does not comprise a surgical step performed on the non-human body.

The method for cell nuclear transfer of the present invention provides a tool for the production of model animals for any relevant disease one could wish to design in order to study the development of disease, potential treatment regimens, drug testing and prevention. The disease of choice is not limited to any particular group of diseases. Examples of use of the present invention for developing genetically modified animal disease models are shown below. However, the invention is not limited to the examples listed below.

The genetic modifications are introduced in the somatic cell prior to SCNT by the HMC technique. However, the genetic modification may in another embodiment be introduced during the hand made cloning (HMC), for example by addition of transgenes at different steps of the HMC procedure that will then find their way to the genome of the embryo.

The genetic modifications comprise random integration of a disease causing gene, mutated gene, into the genome of the somatic cell. It could also be random integration of a normal non-mutated gene that will cause a disease when expressed in a specific tissue or at a specific expression level.

The introduced gene or transgene may originate from any species, including bacteria, pig, human, mouse, rat, yeast, invertebrates, or plants. Regulatory sequences of the transgene may drive ubiquitous or inducible or tissue- and/or time-specific expression and may also originate from any species including pig, human, mouse, rat, yeast, invertebrates, or plants.

Importantly, the genetic modification in the somatic cell may be targeted to a specific region in the porcine genome by homologous recombination of a targeting construct or by gene editing procedures. This could be inactivation (e.g. knock-out) of specific genes that will cause a disease or phenotype, or it could be integration (knock-in) of specific mutations to specific genes that will then cause disease. Also, disease causing transgenes can be integrated into specific regulatory regions of the porcine genome by homologous recombination methods.

The genetic modifications introduced into the porcine genome prior or during the HMC procedure could also be epigenetic modifications (e.g. methylation of DNA or methylation or acetylation/deacetylation of histones) by incubating somatic cells, oocytes or reconstructed HMC embryos with chemical components such as Tricostatin or compounds with similar effect.

The invention relates to genetically modified animals as disease models for example models for degenerative diseases, mitochondria related protein folding disorders, Alzheimer's disease, Parkinson's disease, Huntington's Chorea, or sclerosis. However, also a model of hereditary Alzheimer's disease is an embodiment of the present invention.

In yet other embodiment the disease models may include all kinds of cancer diseases, for example breast cancer. But all cancer diseases could be studied, such as colon cancer, or lung cancer.

Other embodiments relate to models with genetic sensor systems for the analysis of skin penetration of therapeutically active molecules, or flexible liposomes. Yet another embodiment relates to disease models for wound healing, or ulcer treatment. Furthermore disease models for the treatment of malformations for example by reconstructive surgery is within the scope of the present invention. Also disease models related to tissue engineering such as cell transplantation, tissue transplantation, organ transplantation is within the scope of the present invention.

Yet other disease models are psoriasis disease models, and/or disease models for epidermolytic disorders such as Epidermolysis Bullosa Simplex.

Also models for the treatment and prevention of diseases caused by atherosclerosis, ischemic heart disease are embodiments for the present invention.

Models also include models for metabolic disorders which lead to a range of common diseases as for example diabetes, or obesity. But also atherosclerosis and cardiovascular disease may initially be caused by metabolic disorders. Kidney failure is another example of a disease which may be caused by metabolic dysfunction. Likewise, high blood pressure (hypertension) may also be due initially to metabolic dysfunction and can be studied in genetically modified animal models for metabolic disorders. Also disease caused by mutations in mitochondrial proteins, e.g. short chain acyl-coA dehydrogenase deficiency, neuromuscular weakness, degeneration by expression of deleted variant of Ornitine Transcarbamylase.

Vitrification

The term cryopreservation is used for the different cell freezing techniques involved in freezing, storage and the thawing process of living cells. Vitrification is a form of cryopreservation where living cells are rapidly cooled so that the fluid of the cell does not form into ice. Thus, vitrification relates to the process of cooling where cells or whole tissues are preserved by cooling to low sub-zero temperatures, such as (typically) −80 C or −196 C (the boiling point of liquid nitrogen). At these low temperatures, any biological activity, including the biochemical reactions that would lead to cell death is effectively stopped. Vitrification, however, refers to a special approach, where no ice formation is allowed in the medium and the preserved cells or tissues. This ice-free cooling can be achieved by application of high concentrations of cryoprotectant solutions and extremely high cooling rates. Warming should also be performed with rapid increase of the temperature.

One aspect of the present invention relates to the ability of vitrifying (cryopreserving) an oocyte, cytoplast, cells, embryos, or blastocysts. Thus, the present invention discloses a method for cryopreservation of a pig embryo comprising: a) establishing at least one pig oocyte, b) delipating the oocyte, c) activating the reconstructed embryo to form an embryo, d) culturing said embryo, e) vitrifying the embryo. Furthermore the delipated oocyte may be separated into at least two parts as described elsewhere herein, obtaining an oocyte having a nucleus and at least one cytoplast.

In particular the invention relates to the vitrification of an oocyte, however, the invention also relates to the vitrification of embryos, preferably embryos at the blastocyst stage. I one embodiment, the embryo is cultured to blastocyst stage prior to vitrification. Especially pig embryos are covered by the present invention. Also vitrified cytoplasts are covered by the present invention, as are cells.

Yet another aspect of the invention relates to the cryopreservation of a pig embryo derived by a method for cell nuclear transfer as described herein comprising a step of vitrifying a pig embryo. A further aspect of the invention relates to pig embryos obtained, or obtainable by the methods provided herein.

The term 'cryopreserving' as used herein can refer to vitrification of an oocyte, cytoplast, a cell, embryo, or animal of the invention. The temperatures employed for cryopreservation is preferably lower than −80 degree C., and more preferably at temperatures lower than −196 degree C. Oocytes, cells and embryos of the invention can be cryopreserved for an indefinite amount of time. It is known that biological materials can be cryopreserved for more than fifty years.

It is within the scope of the present invention that embryos may be cryopreserved prior to transfer to a host mammal when employing methods for producing a genetically engineered or transgenic non-human mammal. Such cryopreservation prior to transfer may be at the blastocyst stage the of embryo development.

One aspect of the invention relates to the non-invasive delipation of oocytes by mild treatment with an enzymatic agent, for example a pronase. In a preferred embodiment the pronase concentration is preferably in the range of 0.5 to 5 mg/ml, such as 0.5 mg/ml to 3 mg/ml, for example 0.5 mg/ml to 2 mg/ml. Preferably, the pronase has a concentration of 1 mg/ml. In another embodiment of the present invention the non-invasive delipation of oocytes is obtained by treatment with a pronase at concentration of 3.3 mg/ml.

The delipation of oocytes is performed in the presence of a suitable medium, for example a medium comprising 50% cattle serum.

The delipation process is allowed to proceed for a period preferably in the range 1 to 5 min, in particular for 3 min. However, in cases wherein the pronase concentration is in the range of 2.5 mg/ml to 5 mg/ml the period for which the delipation process is allowed to proceed is ranging from 5 sec. to 15 sec, for example 5 sec to 10 sec, such as 10-15 sec. One embodiment of the present invention is the delipation of oocytes using 3.3 mg/ml pronase for 10 sec.

Preferably, the oocytes are subsequently washed in a suitable medium, for example a Hepes-buffered TCM-199 medium, supplemented with calf serum, for example calf serum at 20%. The pronase digested and washed oocytes are preferably subjected to centrifugation at in the range of 8.000 to 15.000×g, for example 9.000 to 14.000×g. In an especially preferred embodiment the oocytes are centrifuged at 12000× g. The centrifugation may proceed for in the range of 10 to 30 min, such as for 20 min.

In an especially preferred embodiment of the present invention the oocytes are delipated by pronase at a concentration of 1 mg/ml for 3 min, after which the oocytes may be washed and subsequently subjected to centrifugation at 12.000×g for 20 min.

In a preferred embodiment of the invention the delipated oocytes may be vitrified. According to one embodiment of the invention the delipated oocytes may be vitrified and subsequently warmed to be employed for the procedures according to the present invention. In an alternative embodiment the delipated oocytes may be used in the methods as described herein to produce for example embryos, in particular embryos at the blastocyst stage which preferably may be vitrified. Vitrified oocytes, cytoplast, cells, embryos or embryos at the blastocyst stage may thus be vitrified. Vitrified blastocysts produced by the vitrification process of the present invention may be stored and upon warming may be implanted in a suitable non-human mammal to produce genetically modified mammals according to the present methods for cell nuclear transfer.

Mitochondria

Cells of the tissue of the genetically modified non-human mammals and/or non-human embryos obtainable by the present invention may harbour mitochondria of different maternal sources. In a preferred embodiment the non-human mammals and/or non-human embryos may harbour mitochondria from only one maternal source, However, in another preferred embodiment the non-human mammals and/or non-human embryos may harbour mitochondria from at least two maternal sources, such as three maternal sources, for example four maternal sources, such as five maternal sources, for example six maternal sources, such as seven maternal sources, for example eight maternal sources, such as nine maternal sources, for example ten maternal sources. The probability of having a specific number of maternal sources can be calculated based on the observed types of mitochondria.

EXAMPLES

Except where otherwise indicated all chemicals were obtained from Sigma Chemical Co. (St Louis, Mo., USA).

Oocyte Collection and In Vitro Maturation (IVM)

Cumulus-oocyte complexes (COCs) were aspirated from 2-6 mm follicles from slaughterhouse-derived sow or gilt ovaries. COCs were matured in groups of 50 in 400 µl bicarbonate-buffered TCM-199 (GIBCO BRL) supplemented with 10% (v/v) cattle serum (CS), 10% (v/v) pig follicular fluid, 10 IU/ml eCG, 5 IU/ml hCG (Suigonan Vet; Skovlunde, Denmark) at 38.5° C. in the "Submarine Incubation System" (SIS; Vajta, et al. 1997) in 5% $CO_2$ in humidified air for 41-44 hours.

In Vitro Fertilization (IVF)

IVF experiments were performed with in vitro matured oocytes in 3 identical replicates. After maturation, COCs were washed twice with mTBM containing 2 mM caffeine ($mTBM_{fert}$) and transferred in groups of 50 to 400 µl $mTBM_{fert}$. Freshly ejaculated semen was treated as described previously (Booth, et al., in press). After 2 h capacitation at 38.5° C. and in 5% $CO_2$ in humidified air, sperm was added to the oocytes with the adjusted final concentration of $1 \times 10^5$ sperm/ml. Fertilization was performed at 38.5° C. and in 5% $CO_2$ in humidified air in the SIS for 3 h. After the insemination, the presumptive zygotes were vortexed in $mTBM_{fert}$ to remove cumulus cells before washing in IVC medium and placing in culture dishes (see Embryo culture and evaluation).

Handmade Cloning (HMC)

The applied HMC method was based on our previous work in cattle and pig (Kragh, et al., 2004; Peura and Vajta, 2003; Vajta, et al., 2003), but with significant modifications. Briefly, at 41 h after the start of maturation, the cumulus investment of the COCs was removed by repeated pipetting in 1 mg/ml hyaluronidase in Hepes-buffered TCM199. From this point (except where otherwise indicated), all manipulations were performed on a heated stage adjusted to 39° C., and all drops used for handling oocytes were of 20 µl volume covered with mineral oil. Oocytes were briefly incubated in 3.3 mg/ml pronase dissolved in T33 (T for Hepes-buffered TCM 199 medium; the number means percentage (v/v) of CS supplement, here 33%) for 5 s. Before the oocytes started to become misshaped in pronase solution, they were picked out and washed quickly in T2 and T20 drops. Oocytes with partially digested but still visible zona were lined up in drops of T2 supplemented with 3 mg/ml polyvinyl alcohol (TPVA) and 2.5 µg/ml cytochalasin B. Trisection instead of bisection was performed manually under stereomicroscopic control with Ultra Sharp Splitting Blades (AB Technology, Pullman, Wash., USA; FIG. 1a). Fragments of trisected oocytes were collected and stained with 5 µg/ml Hoechst 33342 fluorochrome in TPVA drops for 5 min, then placed into 1 µl drops of the TPVA medium on the bottom of a 60 mm Falcon Petri dish covered with oil (3-4 fragments per drop). Using an inverted microscope and UV light, positions of fragments without chromatin staining (cytoplasts) were registered and later collected under a stereomicroscope in T10 drops until the start of the fusion.

Fetal fibroblast cells were prepared as described previously (Kragh, et al., in press). Fusion was performed in two steps where the second one included the initiation of activation, as well. For the first step, one third of the selected cytoplasts (preferably the smaller parts) were used. With a finely drawn and fire-polished glass pipette, 10 cytoplasts were transferred as a group to 1 mg/ml of phytohaemagglutinin (PHA; ICN Pharmaceuticals, Australia) for 3 s, then quickly dropped onto one of the few fibroblast cells individually that were sedimented in a T2 drop. After attachment, 10 cytoplast-fibroblast cell pairs were equilibrated in fusion medium (0.3 M mannitol and 0.01% PVA) for 10 s. Using an alternative current (AC) of 0.6 KV/cm and 700 KHz, cell pairs were aligned to the wire of a fusion chamber (BTX microslide 0.5 mm fusion chamber, model 450; BTX, San Diego, Calif., USA) with the donor cells farthest from the wire (FIG. 1b), then fused with a direct current (DC) of 2.0 KV/cm for 9 µs. After the electrical pulse, cell pairs were removed carefully from the wire, transferred to T10 drops and incubated to observe whether fusion had occurred.

Approximately 1 hour after the first fusion, fused pairs together with the remaining two thirds of cytoplasts were equilibrated in activation medium drops separately (0.3 M mannitol, 0.1 mM $MgSO_4$, 0.1 mM $CaCl_2$ and 0.01% polyvinylalcohol (PVA)). Under a 0.6 KV/cm AC, cytoplast-fused pair-cytoplast triplets were aligned sequentially to the wire in groups of 10, with fused pairs located in the middle (FIG. 1c). A single DC pulse of 0.7 KV/cm for 80 µs was used for the second fusion and initiation of activation. The triplets were then removed from the wire and transferred carefully to T10 drops to check the fusion (FIG. 1d). Reconstructed embryos were incubated in culture medium (see Embryo culture and evaluation) supplemented with 5 µg/ml cytochalasin B and 10 µg/ml cycloheximide for 4 h at 38.5° C. in 5% $CO_2$, 5% $O_2$ and 90% $N_2$ with maximum humidity, then washed thoroughly for 3 times in IVC medium before culture.

Parthenogenetic Activation (PA)

Parthenogenetically activated oocytes were produced either separately or in parallel with HMC. Oocytes were denuded in the same way as above except that a longer incubation in pronase was used to get the zona pellucida completely removed. Zona free (ZF) oocytes were then equilibrated for 10 s in activation medium (0.3 M mannitol, 0.1 mM $MgSO_4$, 0.1 mM $CaCl_2$ and 0.01% PVA) and transferred to the fusion chamber (BTX microslide 0.5 mm fusion chamber, model 450; BTX, San Diego, Calif., USA). A single DC pulse of 0.85 KV/cm for 80 µs was generated with a BLS CF-150/B cell fusion machine (BLS, Budapest, Hungary) and applied to ZF oocytes. For zona intact (ZI) oocytes, a single DC pulse of 1.25 KV/cm for 80 µs was used (according to our unpublished preliminary experiments, these parameters resulted in the highest activation and subsequent in vitro development for ZI and ZF oocytes, respectively). The procedure after the electrical pulse was the same as for HMC reconstructed embryos.

Embryo Culture and Evaluation

All porcine embryos produced by the above treatments were cultured in a modified NCSU37 medium (Kikuchi, et al., 2002) containing 4 mg/ml BSA at 38.5° C. in 5% $O_2$, 5% $CO_2$ and 90% $N_2$ with maximum humidity. The culture medium was supplied with 0.17 mm sodium pyruvate and 2.73 mm sodium lactate from Day 0 (the day for fertilization and activation) to Day 2, then sodium lactate and sodium pyruvate was replaced with 5.5 mm glucose from Day 2 to Day 7. All ZF embryos were cultured in the WOW system (Vajta, et al., 2000) in the same culture medium and gas mixture as used above, with careful medium change on Day 2 without removing the embryos from the WOWs. The blastocyst rate was registered on Day 7. To determine total cell numbers, blastocysts were fixed and mounted to a glass microscopic slide in glycerol containing 20 µg/µl Hoechst 33342 fluorochrome. After staining for 24 h, embryos were observed under a Diaphot 200 inverted microscope with epifluorescent attachment and UV-2A filter (Nikon, Tokyo, Japan).

Example 1

Differences in developmental competence between sow (2.5 years, 170 Kg in weight) derived oocytes and gilt (5.5~6 months, 75 Kg in weight) derived oocytes were investigated through ZF and ZI PA after 44 h in vitro maturation. Four combined groups were investigated in 3 identical replicates: (1) ZF oocytes from sows (2) ZI oocytes from sows (3) ZF oocytes from gilts (4) ZI oocytes from gilts. For ZF activation, a single DC pulse of 0.85 KV/cm for 80 µs was applied, while a single 1.25 KV/cm pulse was used to activate ZI oocytes. Following 7 days culture as described above, the percentage of blastocysts per activated embryo was determined.

The in vitro developmental competence of parthenogenetically activated oocytes derived from either sows or gilts was investigated. As shown in Table 1, the blastocyst rates of parthenogenetically activated oocytes from sows were significantly higher than those from gilts, either after ZF or ZI PA.

TABLE 1

Blastocyst development of Day 7 parthenogenetically activated sow and gilt oocytes

| | Zona Free | | Zona Intact | |
|---|---|---|---|---|
| | No. of activated oocytes | No. of blastocysts (%)* | No. of activated oocytes | No. of blastocysts (%)* |
| sow | 103 | 43(42 ± 4)[a] | 110 | 61(55 ± 6)[c] |
| gilt | 85 | 17(20 ± 2)[b] | 137 | 36(26 ± 5)[d] |

[a,b]Different superscripts mean significant differences (p < 0.05).
[c,d]Different superscripts mean significant differences (p < 0.05).
*Percentage (Mean ± S.E.M) of embryos developed to blastocysts.

The difference in oocytes developmental competence between sows and gilts has been examined in in vitro production (IVP) and somatic cell nuclear transfer (SCNT) embryos separately, resulting in a similar conclusion as in the earlier publication of other research groups (Sherrer, et al., 2004; Hyun, et al., 2003), i.e. that embryos from sow-derived oocytes are superior to those from gilt-derived oocytes in supporting blastocyst development. Although gilts used in our study were at the borderline of maturity, the difference between Day 7 blastocyst rates after PA was significant, proving the superior developmental competence of sow oocytes.

Example 2

The feasibility of modified porcine HMC was investigated in 6 identical replicates, with IVF and in parallel ZF PA as controls. The more competent sow oocytes (according to Example 1) were used in Example 2. Seven days after reconstruction and/or activation, the number of blastocysts per reconstructed embryo and total cell numbers of randomly selected blastocysts were determined.

More than 90% of oocyte fragments derived from morphologically intact oocytes could be recovered for HMC after the trisection. In average, 37 embryos could be recovered out of 100 matured oocytes. The developmental competence of all sources of porcine embryos is shown in Table 2. On Day 7, the development of reconstructed embryos to the blastocyst stage was 17±4% with mean cell number of 46±5, while the blastocyst rates for IVF, and ZF PA were 30±6% and 47±4% (n=243, 170, 97) respectively.

TABLE 2

In vitro development of embryos produced by HMC, IVF and ZF PA

| Embryo origins | No. of embryos/oocytes in culture | No. of blastocysts | blastocyst rates (Mean ± S.E.M). | Mean cell number of blastocysts |
|---|---|---|---|---|
| HMC | 243 | 41 | 17 ± 4[a] | 46 ± 5[d] |
| IVF | 170 | 52 | 30 ± 6[b] | 74 ± 6[e] |
| ZF PA | 97 | 46 | 47 ± 4[c] | 53 ± 7[d] |

[a,b,c]Different superscripts mean significant differences (p < 0.05).
[d,e]Different superscripts mean significant differences (p < 0.05).

Although the theoretical maximum efficiency was still not approached, the integration of zona partial digestion and oocyte trisection almost doubled the number of reconstructed embryos compared to our earlier system (Kragh, et al., 2004 Reprod. Fertil. Dev 16, 315-318). This increase in reconstruction efficiency may have special benefits in porcine cloning since oocyte recovery after aspiration is more demanding and time-consuming than in cattle. An even more important point is the high embryo number required for establishment of pregnancies following porcine nuclear transfer. IVC in pigs is also regarded as a demanding and inefficient procedure (Reed, et al., 1992 Theriogeneology 37, 95-109). A disadvantage of ZF systems is that the embryos have to reach at least the compacted morula or early blastocyst stage in vitro to avoid disintegration in the oviduct without the protective layer of the zona pellucida. On the other hand, once in the blastocyst stage, zona free embryos can be transferred successfully as proved by calves born after either embryonic or somatic cell nuclear transfer (Peura et al., 1998; Tecirlioglu et al., 2004; Oback et al., 2003; Vajta, et al., 2004) and also by the piglets born after zona-free IVP of oocytes (Wu, et al., 2004). NCSU37 medium has been the most widely and successfully used medium for the culture of pig embryos. However, despite the improved embryo development compared with other media, the viability of IVP porcine embryos is still compromised after IVC. Some reports suggested that glucose is not metabolized readily by early porcine embryos before the eight-cell stage but used in higher amounts in embryos between the compacted morula and blastocysts stages (Flood, et al., 1988). The replacement of glucose with pyruvate and lactate in NCSU37 for the first 2 days culture resulted in a blastocyst rate of 25.3% for IVP porcine embryos in Kikuchi's study (Kukuchi, et al., 2002), which was further corroborated by our present studies with an IVP blastocysts rate of 30% in average. Moreover, the first evaluation of this sequential culture system on porcine HMC and ZF PA embryos has resulted in blastocyst rates of 17% and 47% respectively. Sometimes, the blastocyst rate of ZI PA could even reach levels as high as 90% (Du, unpublished)

Statistical Analysis

ANOVA analysis was performed using SPSS 11.0. A probability of $P<0.05$ was considered to be statistically significant.

Example 3

Vitrification of hand-made cloned porcine blastocysts produced from delipated in vitro matured oocytes.

Recently a noninvasive procedure was published for delipation of porcine embryos with centrifugation but without subsequent micromanipulation (Esaki et al. 2004 Biol Reprod. 71, 432-6).

Cryopreservation of embryos/blastocysts was carried out by vitrification using Cryotop (Kitazato Supply Co, Fujinomiya Japan) as described previously (Kuwayama et al. 2005a; 2005b). At the time of vitrification, embryos/blastocysts were transferred into equilibration solution (ES) consisting of 7.5% (V/V) ethylene glycol (EG) and 7.5% dimethylsulfoxide (DMSO) in TCM199 supplemented with 20% synthetic serum substitute (SSS) at 39° C. for 5 to 15 min. After an initial shrinkage, embryos regained their original volume. 4~6 embryos/blastocysts were transferred into 20 ul drop of vitrification solution (VS) consisting of 15% (V/V) EG and 15% (DMSO) and 0.5M sucrose dissolved in TCM199 supplemented with 20% SSS. After incubation for 20 s, embryos were loaded on Cryotop and plunged into liquid nitrogen. The process from exposure in VS to plunging was completed with 1 min.

Embryos/blastocysts were thawed by immersing Cryotop directly into thawing solution (TS) consisting of 1.0M sucrose in TCM199 plus 20% SSS for 1 min, then transferred to dilution solution (DS) consisting of 0.5 M sucrose in TCM199 plus 20% SSS for 3 min. To remove cryoprotectant, embryos/blastocysts were kept twice in a washing solution (WS; TCM199 plus 20% SSS), 5 min for each time. Survival of vitrified blastocysts was determined according to reexpansion rates after 24 h recovery in culture medium supplemented with 10% calf serum (CS).

The non-invasive delipation method was applied to in vitro matured porcine oocytes and further development of delipated oocytes after parthenogenetic activation was investigated in 4 identical replicates. Oocytes were randomly separated into delipation and control groups.

Figure 2:
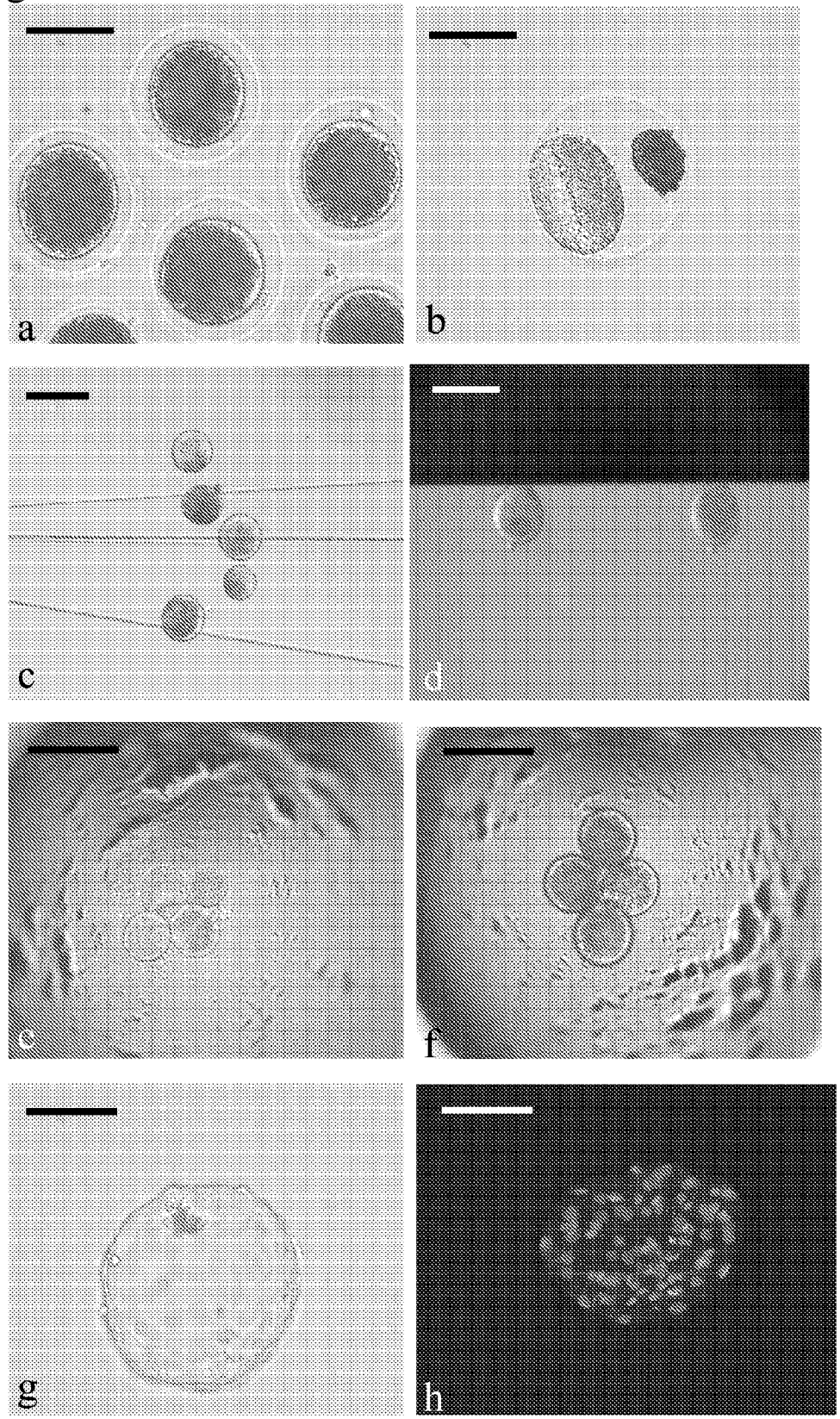
FIG. 2. (a) In vitro matured oocytes after partial zona digestion. (b) Delipated oocytes after centrifugation. (c) Bisection of delipated oocytes. (d) Couplets of fibroblast-oocyte fragment for the first fusion. (e) Four-cell stage reconstructed embryos developed from delipated oocytes. (f) Four-cell stage reconstructed embryos developed from intact oocytes. (g) Re-expanded blastocysts from delipated embryos after warming. (h) Hoechst staining and UV illumination of re-expanded blastocysts from delipated embryos after warming. Bar represents 100 μm.

For delipation, oocytes were digested with 1 mg/ml pronase in the presence of 50% cattle serum (CS) for 3 min, and washed in Hepes-buffered TCM-199 medium supplemented with 20% CS which results in partial zona pellucida digestion (FIG. 2a). Subsequently 40-50 oocytes were centrifuged (12000×g, 20 min) at room temperature in Hepes-buffered TCM-199 medium supplemented with 2% CS, 3 mg/ml PVA and 7.5 µg/ml cytochalasin B (CB) (FIG. 2b). Zonae pellucidea of both centrifuged and intact oocytes were removed completely with further digestion in 2 mg/ml pronase solution.

For activation, a single direct current of 85 Kv/cm for 80 us was applied to both groups, followed by 4 h treatment with 5 µg/ml CB and 10 µg/ml cycloheximide (CHX). All embryos were then cultured in the modified NCSU37 medium. Day 7 blastocysts were vitrified and warmed by using the Cryotop technique (Kuwayama et al., RBM Online, in press) at 38.5° C. Survival of vitrified blastocysts was determined according to reexpansion rates after 24 h recovery in culture medium supplemented with 10% CS. Cell numbers of reexpanded blastocysts from both groups were determined after Hoechst staining. Results were compared by ANOVA analysis. Partial zona digestion and centrifugation resulted in successful delipation in 173/192 (90%) of oocytes. The development to blastocysts was not different between delipated and intact oocytes (28±7% vs. 28±5% respectively; P>0.05). However, survival rates of blastocysts derived from delipated oocytes were significantly higher than those developed from intact oocytes (85±6% vs. 32±7% respectively; P<0.01). There is no difference in average cell number of reexpanded blastocysts derived from either delipated or intact oocytes (36±7 vs. 38±9, respectively; P>0.05). The results demonstrate that the simple delipation technique does not hamper the in vitro development competence of activated porcine oocytes, and improves the cryosurvival of the derived blastocysts without significant loss in cell number.

After delipation, zona pellucida of oocytes from both groups was removed completely. The same parameters as described above for electrical activation were applied to both groups. Seven days after activation, blastocyst rates and blastocyst cell numbers were determined.

The feasibility of applying a non-invasive delipation technique to in vitro matured porcine oocytes was investigated. 90% (173/192) oocytes can be delipated successfully. As shown in table 3, the development to blastocysts was not different between delipated and intact oocytes (28±7% vs. 28±5% respectively; P>0.05). However, survival rates of blastocysts derived from delipated oocytes were significantly higher than those developed from intact oocytes (85±6% vs. 32±7% respectively; P<0.01). There is no difference in average cell number of reexpanded blastocysts derived from either delipated or intact oocytes (36±7 vs. 38±9, respectively; P>0.05).

TABLE 3

Developmental competence and cryosurvival of vitrified-thawed embryos from delipated and intact activated oocytes.

| Oocyte treatment | Activated oocyte | Blastocyst rate (%) | Reexpanded blastocyst after warming (%) | Mean cell number of reexpanded blastocysts |
| --- | --- | --- | --- | --- |
| Delipated | 173 | 28 ± 7 | 85 ± 6 | 36 ± 7 |
| Intact | 156 | 28 ± 5 | 32 ± 7 | 39 ± 9 |

Handmade Cloning of Delipated Oocytes

Delipated oocytes were used for HMC in 5 replicates. Four identical replicates of non-delipated oocytes for HMC were used as a control system. Seven days after reconstruction, blastocysts produced from both groups were vitrified with Cryotop. Survival rates and cell numbers of re-expanded blastocysts were determined as described for the blastocysts produced by PA.

Except where otherwise indicated, all manipulations were performed on a heated stage adjusted to 39° C., and all drops used for handling oocytes were of 20 µl volume covered with mineral oil. For somatic cell nuclear transfer, the handmade cloning (HMC) described in our previous work (Du, et al., 2005) was applied with a single modification: for enucleation of both delipated and control oocytes, bisection instead of trisection was applied.

Briefly, after the removal of cumulus investment, control oocytes were incubated in 3.3 mg/ml pronase dissolved in T33 for 10 s. Before the oocytes started to become misshaped in pronase solution, they were picked out and washed quickly in T2 and T20 drops. Delipated oocytes after centrifugation were digested in the 3.3 mg/ml pronase solution for an additional 5 s.

Both control and delipated oocytes with partially digested, distended and softened zonae pellucidae were lined up in T2 drops supplemented with 2.5 µg/ml cytochalasin B. Bisection was performed manually under stereomicroscopic control (FIG. 2c) with Ultra Sharp Splitting Blades (AB Technology, Pullman, Wash., USA). Halves were collected and stained with 5 µg/ml Hoechst 33342 fluorochrome in T2 drops for 5 min, and then placed into 1 µl drops of T2 medium on the bottom of a 60 mm Falcon Petri dish covered with oil (3-4 halves per drop). Using an inverted microscope and UV light, positions of halves without chromatin staining (cytoplasts) were registered. Cytoplasts were later collected under a stereomicroscope and stored in T10 drops.

Porcine foetal fibroblast cells were prepared with trypsin digestion from monolayers as described previously (Kragh, et al., 2005). Fusion was performed in two steps where the second one included the initiation of activation, as well. For the first step, 50% of the available cytoplasts were transferred into 1 mg/ml of phytohaemagglutinin (PHA; ICN Pharmaceuticals, Australia) dissolved in T0 for 3 s, then quickly dropped over single fibroblast cells. After attachment, cytoplast-fibroblast cell pairs were equilibrated in fusion medium (0.3 M mannitol and 0.01% PVA) for 10 s and transferred to the fusion chamber. Using an alternating current (AC) of 0.6 KV/cm and 700 KHz, pairs were aligned to the wire of a fusion chamber with the somatic cells farthest from the wire (FIG. 2d), then fused with a direct current of 2.0 KV/cm for 9 µs. After the electrical pulse, cell pairs were removed carefully from the wire, transferred to T10 drops and incubated to observe whether fusion had occurred.

Approximately 1 hour after the first fusion, each pair was fused with another cytoplast in activation medium. AC current and a single DC pulse of 0.7 KV/cm for 80 µs were applied as described above. Fusion was detected in T10 drops, then reconstructed embryos were transferred into IVC0-2 medium (see Embryo culture and evaluation) supplemented with 5 µg/ml cytochalasin B and 10 µg/ml cycloheximide. After a 4 h incubation at 38.5° C. in 5% $CO_2$, 5% $O_2$ and 90% $N_2$ with maximum humidity, embryos were washed 3 times in IVC0-2 medium before culture.

TABLE 4

Developmental competence and cryosurvival of vitrified-thawed embryos of SCNT porcine embryos derived from delipated and intact oocytes.

| HMC group | No. of reconstructed embryos | Blastocyst rate (%)* | Reexpanded blastocyst after warming (%)* | Mean cell number of reexpanded blastocysts* |
|---|---|---|---|---|
| Delipated | 240 | 21 ± 6$^a$ | 79 ± 6$^b$ | 41 ± 7$^d$ |
| Intact | 150 | 23 ± 6$^a$ | 32 ± 8$^c$ | 39 ± 5$^d$ |

Different superscripts mean significant differences (p < 0.05).
*mean ± S.E.M.

In vitro developmental competence was observed in HMC with delipated oocytes when Day 7 blastocyst rates were compared with control HMC group (21±6% vs. 23±6% respectively; P>0.05; Table 4). Cryosurvival rate after vitrification of cloned blastocysts derived from delipated oocytes was significantly higher than those developed from intact oocytes (79±6% vs. 32±8, respectively; P<0.01).

Example 4

Chemically Assisted Handmade Enucleation (CAHE) and Comparison to Existing Methods After 41-42 h maturation in vitro, COCs were further cultured for 45 min in the same solution supplemented by 0.4 µg/ml demecolcine. Cumulus cells were then removed by pipetting in 1 mg/ml hyaluronidase dissolved in Hepes-buffered TCM-199. From this point (except where otherwise indicated), all manipulations were performed on a heated stage adjusted to 39° C. All drops used for handling oocytes were of 20 µl in volume, and were covered with mineral oil.

Figure 3:
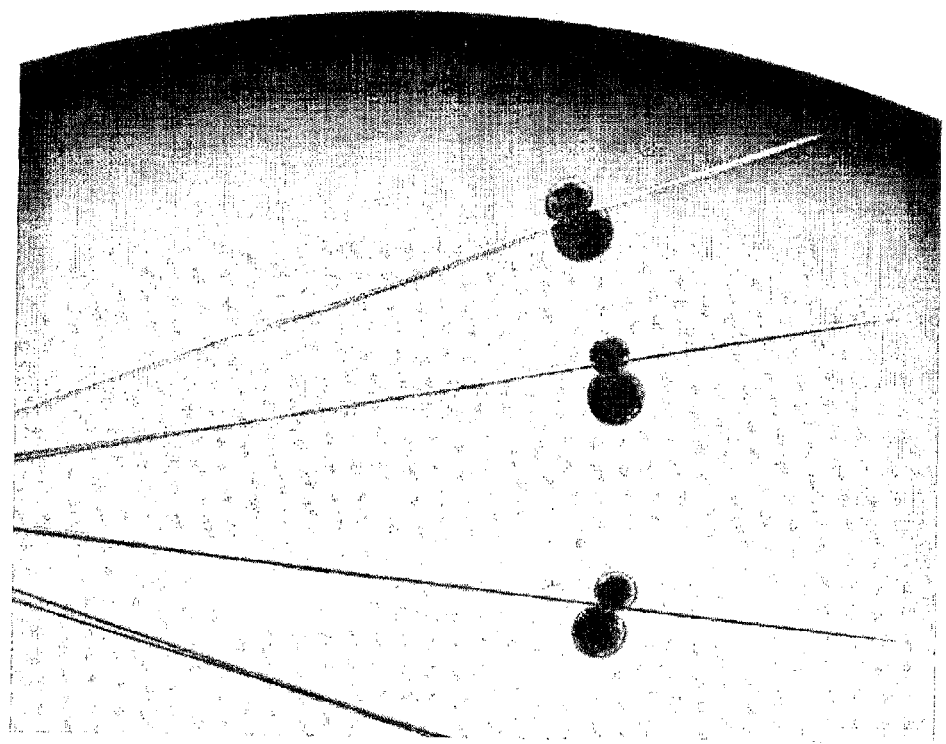
FIG. 3. Bisection at chemically assisted enucleation. Note the extrusion cone or polar body connected to the smaller part (putative karyoplast). Stereomicroscopic picture. Bar represents 50 μm.

Basic steps of the HMC procedure have been described elsewhere herein. Briefly, oocytes without cumulus cells were incubated in 3.3 mg/ml pronase dissolved in T33 (T for Hepes-buffered TCM 199 medium; the number means percentage [v/v] of CS supplement, here 33%) for 20 s. When partial lyses of zonae pellucidae and slight deformation of oocytes occurred, they were picked up and washed quickly in T2 and T20 drops. Nine oocytes were lined up in one T2 drop supplemented with 2.5 µg/ml cytochalasin B (CB). By using a finely drawn and fire-polished glass pipette, oocytes were rotated to find a light extrusion cone and/or strongly attached polar body on the surface, and oriented bisection was performed manually under stereomicroscopic control with a microblade (AB Technology, Pullman, Wash., USA). Less than half of the cytoplasm (close to the extrusion or PB) was separated from the remaining part (FIG. 3). After bisection of all 9 oocytes in the drop, larger parts and smaller parts (with the extrusion or attached PB) were collected and placed into separate drops of T2, respectively.

Oriented Handmade Enucleation without Demecolcine Treatment (OHE)

All steps were similar to the previously described procedure, but demecolcine preincubation was not applied.

Random Handmade Bisection for Enucleation (RHE)

Demecolcine preincubation was omitted from the pretreatment of this group, as well.

After removal of cumulus cells, zonae pellucidae were partially digested by pronase as described above. Random handmade equal bisection was applied in drops of T2 supplemented with 2.5 µg/ml CB. All demi-oocytes were selected and stained with 10 µg/ml Hoechst 33342 in T2 drops for 10 min, then placed into 1 µl drops of T2 medium covered with mineral oil (three demi-oocytes into each drop). Using an inverted microscope and UV light, the positions of chromatin free demi-oocytes, i.e. cytoplasts were registered. These cytoplasts were later collected under a stereomicroscope and stored in T2 drops before further manipulations.

Fusion and Initiation of Activation

Porcine fetal fibroblast cells were prepared as described previously (Kragh, et al., 2005, Du, et al., 2005). Fusion was performed in two steps, where the second one included the initiation of activation as well. For the first step, with a finely drawn and fire-polished glass pipette, approximately 100 somatic cells were placed into a T2 drop, and 20-30 cytoplasts were placed into a T10 drop. After a short equilibration, groups of 3 cytoplasts were transferred to 1 mg/ml of phytohaemagglutinin (PHA) for 2-3 sec, then each was quickly dropped over a single somatic cell. Following attachment, cytoplast-somatic cell pairs were picked up again and transferred to a fusion medium (0.3 M mannitol supplemented with 0.01% [w/v] PVA). By using an alternative current (AC) of 0.6 KV/cm and 700 KHz, equilibrated pairs were aligned to one wire of a fusion chamber (BTX microslide 0.5 mm fusion chamber, model 450; BTX, San Diego, Calif.) with the somatic cells farthest from the wire, then fused with a single direct current (DC) impulse of 2.0 KV/cm for 9 μsec. Pairs were then removed carefully from the wire to a T10 drop, and incubated further to observe whether fusion had occurred.

Approximately 1 h after the fusion, fused pairs and the remaining cytoplasts were separately equilibrated in activation medium (0.3 M mannitol, 0.1 mM MgSO$_4$, 0.1 mM CaCl$_2$, supplemented with 0.01% [w/v] PVA). By using a 0.6 KV/cm AC, one pair and one cytoplast was aligned to one wire of the fusion chamber, with fused pairs contacting the wire. A single DC pulse of 0.86 KV/cm for 80 μsec was used for the second fusion and initiation of activation. Fusion was checked in after incubation in T10 drops.

Traditional Cloning (TC)

Micromanipulation was conducted with a Diaphot 200 inverted microscope (Nikon, Tokyo, Japan), as described before (Chen et al., 1999; Zhang et al., 2005). Briefly, after 42-44 h in vitro maturation, the cumulus cells were removed as described above. All manipulations were performed on a heated stage adjusted to 39° C. A single 50 μL micromanipulation solution drop was made in the central area on a lid of 60 mm culture dish and covered with mineral oil. Groups of 20-30 oocytes and fetal fibroblast cells were placed in the same drop. After incubation for 15-30 min, the oocyte was secured with a holding pipette (inner diameter=25-35 μm and outer diameter=80-100 μm). After being placed at the position of 5-6 o'clock, the first polar body and the adjacent cytoplasm (approx. 10% of the total volume of the oocyte) presumptively containing metaphase plate were aspirated and removed with a beveled injection pipette (inner diameter=20 μm). A fetal fibroblast cell was then injected into the space through the same slit. After nuclear transfer (NT), reconstructed couplets were transferred into drops of media covered with mineral oil for recovery for 1-1.5 h until fusion and activation was conducted. The recovery medium was NCSU-23 supplemented with 4 mg/mL BSA and 7.5 μg/mL CB. Reconstructed couplets were incubated in fusion medium for 4 min. Couplets were aligned manually using a finely pulled and polished glass capillary to make the contact plane parallel to electrodes. A single, 30 μsec, direct current pulse of 2.0 kV/cm was then applied. After culture in drops of IVC0-2 (specified in "Embryo culture and evaluation") supplemented with 7.5 μg/mL CB for 30-60 min, fusion results were examined under a stereomicroscope. Fused couplets were subjected to a second pulse in activation solution. After 30 min incubation in T10 they were transferred to IVC0-2 to evaluate in vitro development.

Further Steps of Activation

After the activation impulse, all reconstructed embryos were incubated in IVC0-2 supplemented with 5 μg/ml CB and 10 μg/ml cycloheximide at 38.5° C. in 5% CO$_2$, 5% O$_2$, and 90% N$_2$, with maximum humidity.

Embryo Culture and Evaluation 4 h later, all reconstructed and activated embryos were washed and cultured in Nunc four-well dishes in 400 μl IVC0-2 covered by mineral oil at 38.5° C. in 5% CO$_2$, 5% O$_2$, and 90% N$_2$, with maximum humidity. IVC0-2 was a modified NCSU37 medium (Kikuchi, et al., 1999), containing 4 mg/ml BSA, 0.17 mM sodium pyruvate, and 2.73 mM sodium lactate from Day 0 (the day for activation) to Day 2. Sodium pyruvate and sodium lactate were replaced with 5.5 mM glucose from Day 2 to Day 7 (IVC2-7). All zonae free embryos were cultured in the Well of the Well (WOW) system (Vajta et al., 2000) in the same culture medium and gas mixture as used above, with careful medium change on Day 2 without removing the embryos from the WOWs. TC embryos were cultured in groups of 15 to 30 in wells of four-well dishes by using the same medium amount and composition. Cleavage and blastocyst rates were registered on Day 2 and Day 7, respectively. To determine total cell numbers, blastocysts were fixed and mounted to a glass microscope slide in a small amount (<2 μl) of glycerol containing 10 μg/ml Hoechst 33342. After staining for several hours at room temperature, embryos were observed under a Diaphot 200 inverted microscope with epifluorescent attachment and UV-2A filter (Nikon, Tokyo, Japan).

Comparison of Efficiency of CAHE vs. OHE

Figure 4:
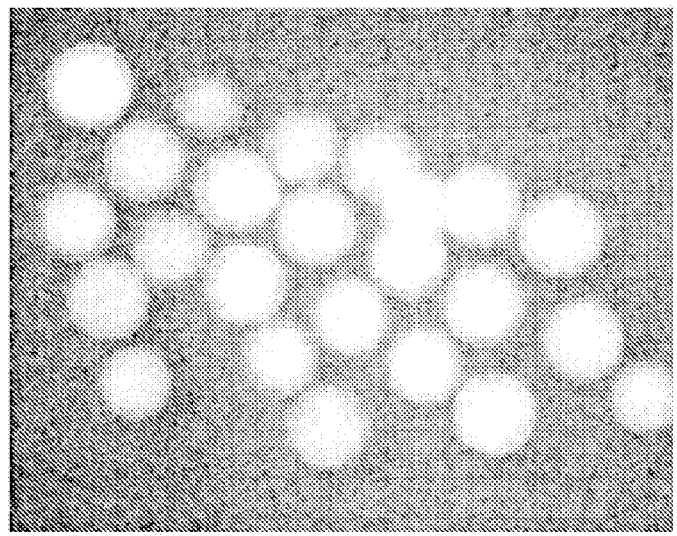
FIG. 4. Hoechst staining and UV illumination of the absence and presence of chromatin. UV light, inverted fluorescent microscopic picture. Bar represents 50 μm. (a) The absence of chromatin in putative cytoplasts (b) The presence of chromatin in putative karyoplasts.
Figure 4:
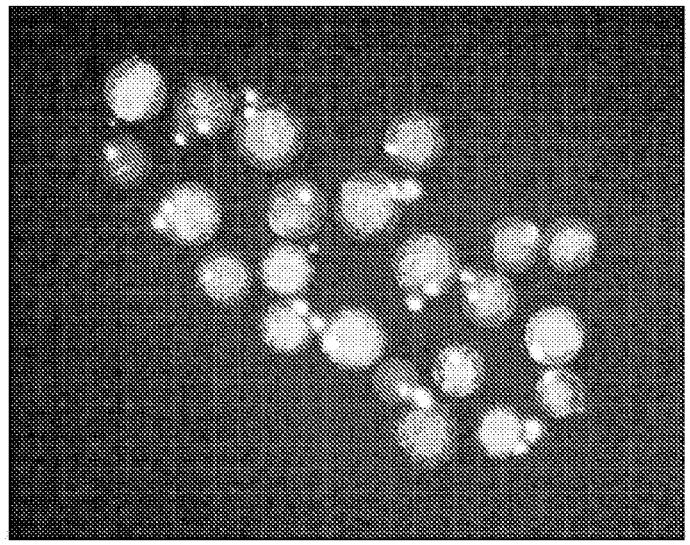

The efficiency and reliability of CAHE was tested in 12 identical replicates by using a total of 620 oocytes. After 41-42 h maturation, oocytes were subjected to demecolcine incubation. Oriented bisection was performed in oocytes where an extrusion cone and/or a strongly attached PB was detected after partial pronase digestion. Percentages of bisected vs. total oocytes and surviving vs. bisected oocytes were registered. Subsequently both putative cytoplasts and karyoplasts were collected separately and stained with Hoechst 33342 (10 μg/ml in T2 for 10 min). The presence or absence of chromatin was detected under an inverted fluorescent microscope (FIG. 4).

The efficiency and reliability of OHE was investigated in 9 identical replicates using a total of 414 oocytes. After 42-43 h in vitro maturation, oriented bisection was performed in matured oocytes where an extrusion cone and/or a PB was detected after partial pronase digestion. Results were evaluated as described in the previous paragraph.

The results are shown in Table 5.

TABLE 5

The efficiency of chemically assisted handmade enucleation (CAHE) and oriented handmade enucleation (OHE)

| Groups | No. of treated oocytes | Bisected/total oocytes (%)* | Cytoplast/ bisection (%)* | Cytoplast/ total oocyte (%)* |
|---|---|---|---|---|
| CAHE | 620 | 96 ± 1$^a$ | 94 ± 2$^b$ | 90 ± 3$^c$ |
| OHE | 414 | 92 ± 2$^a$ | 88 ± 3$^b$ | 81 ± 4$^d$ |

*mean ± A.D. (absolute deviations)
Different superscripts mean difference (P < 0.05)

No differences between groups regarding extrusion cones and/or attached polar bodies allowing oriented bisection or in the lysis rates were detected, and the successful enucleation per bisected oocyte ratio was also similar. However the overall efficiency of the procedure measured by the cytoplast per total oocyte number was higher in the CAHE than in the OHE group.

Comparison of in vitro development of embryos produced with CAHE, RHE and TC

In 8 replicates, a total of 468 in vitro matured oocytes were randomly distributed and subjected to three of the enucleation procedures described above. Fusion rates between cytoplast and donor fibroblasts were registered. Reconstructed embryos were activated and cultured as described earlier. Cleavage and blastocyst rates were determined on Day 2 and Day 7, respectively. Stereomicroscopic characteristics of the developed blastocysts were compared between groups.

TABLE 6

Developmental competence of embryos derived from chemically assisted handmade enucleation (CAHE), random handmade enucleation (RHE) and traditional, micromanipulator based cloning (TC).

| Groups | No. of reconstructed embryos | Fusion rate (%)* | Cleavage rate (%)* | Blastocyst rate (%)* | Cell no. of blastocysts (Day 7) |
|---|---|---|---|---|---|
| CAHE | 150 | 87 ± 7$^a$ | 97 ± 6$^b$ | 28 ± 9$^d$ | 57 ± 6$^e$ |
| RHE | 86 | 81 ± 4$^a$ | 87 ± 8$^b$ | 21 ± 9$^d$ | 49 ± 7$^e$ |
| TC | 178 | 81 ± 10$^a$ | 69 ± 9$^c$ | 21 ± 6$^d$ | 53 ± 6$^e$ |

*mean ± A.D. (absolute deviations)
Different superscripts mean difference (P < 0.05).

Fusion rates after enucleation were similar between CAHE, RHE and TC, respectively. The second fusion and activation resulted in negligible (<1%) losses in the first two groups. Although TC resulted in lower cleavage per reconstructed embryo rates than the other two groups, this difference was not present in the blastocyst per reconstructed embryo rates.

Figure 5:
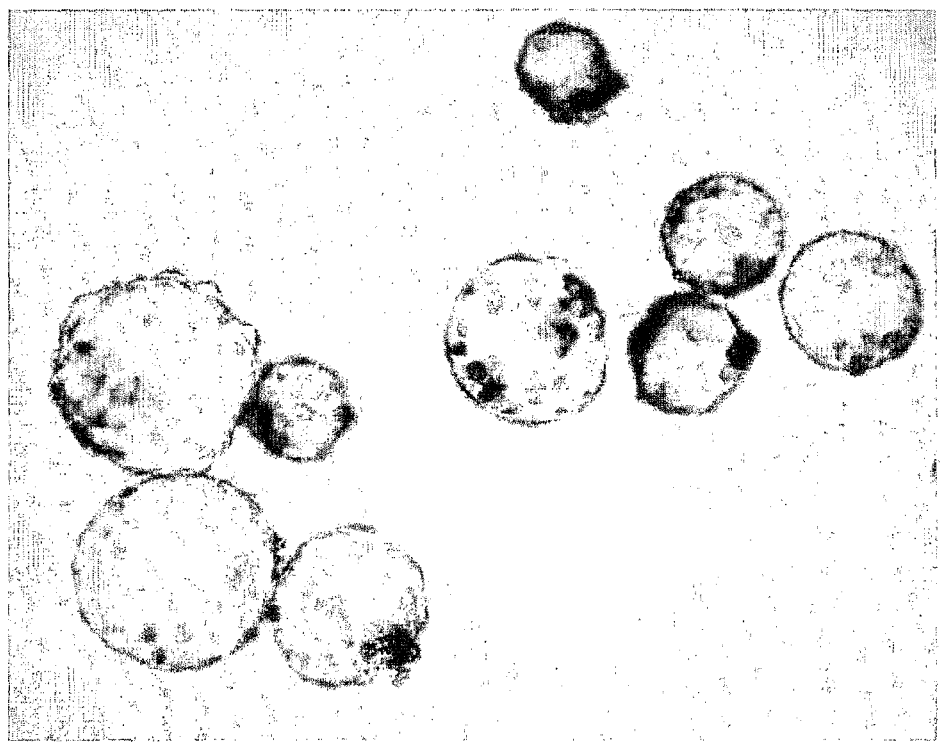
FIG. 5. Stereomicroscopic picture of Day 7 blastocysts produced with chemically assisted handmade enucleation (CAHE). Bar represents 50 μm.
Figure 6:
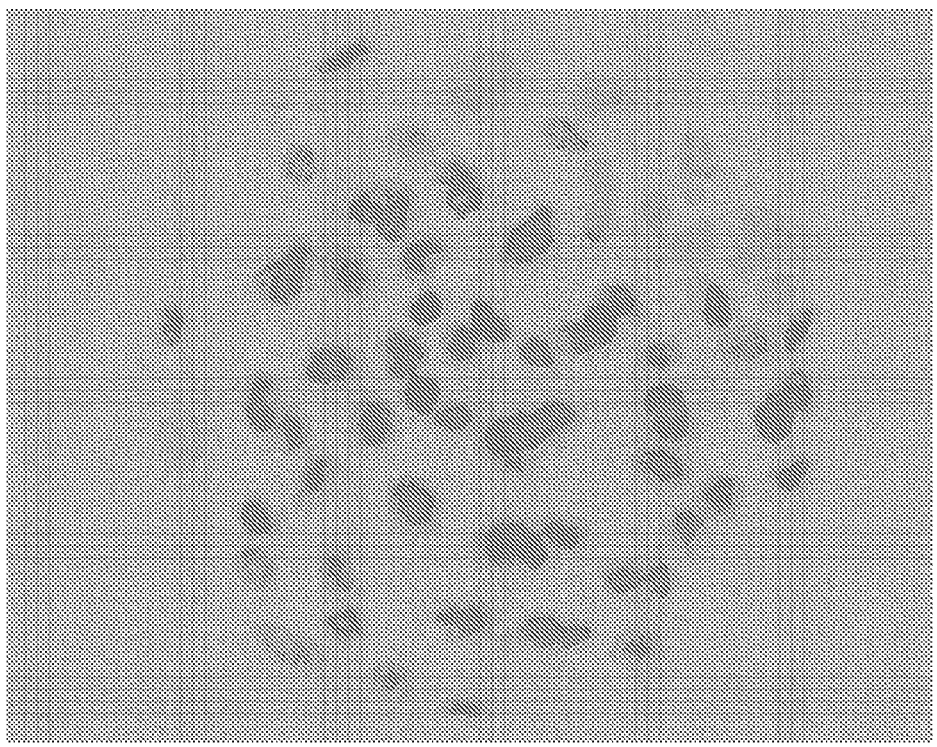
FIG. 6. Hoechst staining and UV illumination of blastocyst developed after chemically assisted handmade enucleation (CAHE). Bar represents 50 μm.

Stereomicroscopic characteristics (size; estimated proportion and outlines of the inner cell mass) did not differ between groups. Cell numbers (57±6 vs. 49±7 vs. 53±6) of the produced blastocysts from CAHE, RHE and TC are shown in Table 6, FIG. 5 and FIG. 6.

Statistical Analysis

AVEDEV was performed by Microsoft XP Excel software and ANOVA was performed by SAS system. A probability of P<0.05 was considered to be statistically significant.

Example 5

Production of Piglets

Handmade Cloning (HMC)

Forty one hrs after the start of in vitro maturation, the cumulus investment of the COCs was removed by repeated pipetting in 1 mg/ml hyaluronidase in Hepes-buffered TCM199. From this point (except where otherwise indicated) all manipulations were performed on a heated stage adjusted to 39° C., and all drops used for handling oocytes were of 20 µl volume covered with mineral oil. Oocytes were briefly incubated in 3.3 mg/ml pronase dissolved in T33 (T for Hepes-buffered TCM 199 medium; the number means percentage (v/v) of calf serum (CS) supplement, here 33%) for 20 sec and then quickly washed in T2 and T20 drops. Oocytes with partially digested but still visible zona were lined up in drops of T2 supplemented with 2.5 µg/ml cytochalasin B (CB). With a finely drawn and fire-polished glass pipette, oocytes were rotated to find the polar body (PB) on the surface, and oriented bisection was performed manually under stereomicroscopic control with a microblade (AB Technology, Pullman, Wash., USA). Thus, less than half of the oocyte cytoplasm (close to the extrusion or PB) was removed from the remaining putative cytoplast. Cytoplasts were washed twice in T2 drops and collected in a T10 drop.

Fetal fibroblast cells were prepared as described previously (Kragh, P. M. et al. *Theriogenology* 64, 1536-1545 (2005).

Fusion was performed in two steps where the second one included the initiation of activation, as well. For the first step, halves of putative cytoplasts were used. With a finely drawn and fire-polished glass pipette, 10 cytoplasts were transferred as a group to 1 mg/ml of phytohaemagglutinin (PHA; ICN Pharmaceuticals, Australia) for 3 sec, then quickly dropped individually onto one of the few fibroblast cells that were sedimented in a T2 drop. After attachment, 10 cytoplast-fibroblast cell pairs were equilibrated in fusion medium (0.3 M mannitol and 0.01% PVA) for 10 sec. Using an alternative current (AC) of 0.6 KV/cm and 700 KHz, cell pairs were aligned to the wire of a fusion chamber (BTX microslide 0.5 mm fusion chamber, model 450; BTX, San Diego, Calif., USA) with the somatic cells farthest from the wire, then fused with a direct current (DC) of 2.0 KV/cm for 9 µsec. After the electrical pulse, cell pairs were removed carefully from the wire, transferred to T10 drops and incubated to observe whether fusion had occurred.

Approximately 1 hr after the first fusion, fused pairs together with the remaining cytoplasts were equilibrated in activation medium drops separately (0.3 M mannitol, 0.1 mM MgSO$_4$, 0.1 mM CaCl$_2$ and 0.01% PVA). Under a 0.6 KV/cm AC, cytoplast-fused pair were aligned sequentially to the wire in groups of 10, with fused pairs far from the wire. A single DC pulse of 0.7 KV/cm for 80 µsec was used for the second fusion and initiation of activation. The pairs were then removed from the wire and transferred carefully to T10 drops to check the fusion. Reconstructed embryos were incubated in PZM-3 medium supplemented with 5 µg/ml CB and 10 µg/ml cycloheximide for 4 hr at 38.5° C. in 5% CO$_2$, 5% O$_2$ and 90% N$_2$ with maximum humidity, then washed thoroughly before culture.

Traditional Cloning (TC)

Micromanipulation was conducted with a Diaphot 200 inverted microscope (Nikon, Tokyo, Japan). Cumulus cells were removed as described above after 42 to 44 hr maturation. All manipulations were performed on a heated stage adjusted to 39° C. A single 50 µL drop of micromanipulation solution (NCSU-23 supplemented with 4 mg/mL BSA and 7.5 µg/mL CB) was made in the central area on a lid of 60 mm culture dish and covered with mineral oil. Groups of 20 to 30 oocytes and fetal fibroblast cells were placed in the same drop. After incubation for 15 to 30 min, one oocyte was secured with a holding pipette (inner diameter=25-35 µm and outer diameter=80-100 µm). After being placed at the position of 5-6 o'clock, the first polar body and the adjacent cytoplasm (approx. 10% of the total volume of the oocyte) presumptively containing metaphase plate were aspirated and removed with a beveled injection pipette (inner diameter=20 µm). A fetal fibroblast cell was then injected into the space through the same slot. After nuclear transfer (NT), reconstructed couplets were transferred into drops of media covered with mineral oil for recovery for 1 to 1.5 hrs until fusion and activation was conducted. Reconstructed couplets were incubated in fusion medium for 4 min. Couplets were aligned manually using a finely pulled and polished glass capillary to make the contact plane parallel to electrodes. A single, 30 µsec, direct current pulse of 2.0 kV/cm was then applied. After culture in drops of PZM-3 medium supplemented with 7.5 µg/mL CB for 30-60 min, fusion results were examined under a stereomicroscope. Fused couplets were subjected to a second pulse in activation solution. After 30 min incubation in T10 they were transferred to PZM-3 medium to evaluate in vitro development.

Embryo Culture and Transfer

Reconstructed embryos were cultured in PZM-3 medium (Dobrinsky, J. T. et al. *Biol Reprod* 55, 1069-1074 (1996) supplemented with 4 mg/ml BSA. Zona-free embryos produced from HMC were cultured in the modified WOWs system (Feltrin, C. Et al. *Reprod Fertil Dev* 18, 126 (2006). Two different cell lines (LW1-2 for HMC, LW2 for TC) were used as nuclear donor cells for HMC and TC to allow the identification of the offspring from the two procedures. LW1-2 and LW2 originate from fetuses from a cross (with Duroc) and pure Danish landrace, respectively.

The average blastocyst per reconstructed embryo rate after in vitro culture for 7 days was 50.1±2.8% (mean±S.E.M), which is significantly higher (p<0.01) for HMC than that of TC performed in parallel in our laboratory (Table 7) and also the highest one that has ever been reported in pig cloning.

TABLE 7

In vitro development of embryos produced from handmade cloning and traditional cloning

| Group | Somatic cell donor | No. of reconstructed embryos | Cleavage rate (%) | Blastocyst rate (%) |
|---|---|---|---|---|
| HMC | LW1-2 | 643 | 83.7 ± 4.90$^a$ | 50.06 ± 2.80$^a$ |
| TC | LW2 | 831 | 74.86 ± 13.16$^b$ | 28.98 ± 2.84$^b$ |

$^{a,b}$Values of different superscripts within columns are significantly different (p < 0.05).
*mean ± S.E.M.

Mixed blastocysts produced from both HMC and TC were surgically transferred to 11 naturally synchronized sows on Day 4 or 5 of estrous cycle. Six (55%) recipients were diagnosed pregnant by ultrasonography, 2 aborted and by the time of writing 2 have delivered 3 and 10 piglets, respectively. A litter size of 10 cloned piglets is, according to our knowledge, the largest litter size so far achieved in pig cloning. All of them are healthy and behave normally except one showed rigid flexure of distal joint of one foreleg. %).

Preliminary results suggest that when embryos of similar stages were transferred, recipients on Day 4 of the estrous cycle supported pregnancy establishment better than those of Day 5 (Table 8).

For the second recipient, the offspring per embryo rate (22%) was the highest one ever reported so far in pig cloning (Walker, S. C. et al. *Cloning Stem Cells* 7, 105-112 (2005); Hoshino, Y. et al. *Cloning Stem Cells* 7, 17-26 (2005)). Comparable live birth/transferred embryo efficiencies were obtained in HMC (17%) and TC (15%).

Statistical Analysis

Differences between the experimental groups were evaluated using independent-samples t-test by SPSS 11.5. P<0.05 was considered significant.

Example 6

One example of a transgene that could be used to produce a transgenic non-human mammal as a disease model for epidermolysis bullosa simplex is the human keratin 14 gene, comprising a mutation as shown below in bold.

The sequence of the transgene integrated in porcine fetal fibroblasts (donor cell) comprises the human keratin 14 promoter and keratin 14 cDNA including start and stop codons (in bold) and the disease causing mutation (in bold and underlined) as described by Sørensen et al., J Invest Dermatol. 1999 February; 112(2):184-90). The fragment is cloned into pN1-EGFP (clontech) containing polyA signal for gene expression and a Neomycin selection gene for selection of cell clones with the transgene integrated.

```
aagcttatat tccatgctag ggttctggtg ttggtgcgtg gggttggggt gggactgcag aagtgccttt taagattatg tgattgactg atctgtcatt ggttccctgc catctttatc
```

TABLE 8

In vivo development of cloned porcine embryos

| Recipient number | Embryos transferred HMC embryo | Embryos transferred TC embryo | Embryo stage (Day) | Recipient cycle (Day) | Pregnancy status | piglets from HMC | No. piglets from TC | Gestation length (Day) |
|---|---|---|---|---|---|---|---|---|
| 1327 | 22 | 10 | D 5, 6, 7 | 4 | Y | 2 | 1 | 116 |
| 1539 | 36 | 10 | D 7 | 4 | Y | 8 | 2 | 115 |
| 1309 | 30 | 28 | D 5, 6 | 4 | Y | | | |
| 1553 | 45 | 44 | D 5, 6 | 4 | Y | | | |
| 1668 | 48 | 18 | D 5, 6 | 5 | Y, aborted | | | |
| 1428 | 78 | 22 | D 5, 6 | 5 | Y, aborted | | | |
| 1725 | 44 | 4 | D 5, 6, 7 | 5 | N | — | — | — |
| 1643 | 22 | 11 | D 5, 6, 7 | 4 | N | — | — | — |
| 1520 | 30 | 26 | D 5, 6 | 4 | N | — | — | — |
| 1363 | 37 | 7 | D 6, 7 | 5 | N | — | — | — |
| 1560 | 99 | 42 | D 5, 6, 7 | 5 | N | — | — | — |

Microsatellite Analysis

Parental analysis using 10 different porcine microsatellite markers confirmed the identical genotype of cloned piglets and donor cells used for nuclear transfer. Identification was done by microsatellite analysis of genomic DNA from each of the newborn piglets, the surrogate sow, and the donor skin fibroblasts LW1-2 and LW2 originating from two fetuses that represent Danish landrace and Duroc, respectively. Ten polymorphic microsatellite loci (SW886, SW58, SW2116, SW1989, SW152, SW378, KS139, SO167, SW1987, SW957) located on different porcine chromosomes were amplified by 3-color multiplex PCR and the products analyzed on the Genetic Analyzer 3130 X1 (Applied Biosystems) using the program Gene Mapper 3.7.

```
-continued
ttttggattc ccctcggagg aggggaggaa ggagtttctt ttgggtttta ttgaatcaaa tgaaagggaa agtagaggtg ttcctatgga ggggaggaag gagtttcttt tgggttttat tgaatcaaat gaaagggaaa gtagaggtgt tcctatgtcc cgggctccgg agcttctatt cctgggccct gcataagaag gagacatggt ggtggtggtg gtgggtgggg gtggtggggc acagaggaag ccgatgctgg gctctgcacc ccattcccgc tcccagatcc ctctggatat agcacccct ccagtgagca
```

```
cagcctcccc ttgcccaca gccaacagca acatgcctcc
caacaaagca tctgtccctc agccaaaacc cctgttgcct
ctctctgggg aaattgtagg gctgggccag ggtgggggga
ccattctctg cagggagatt aggagtgtct gtcaggggcg
ggtggagcgg ggtggggccc tggcttactc acatccttga
gagtcctttg ctggcagatt tggggagccc acagctcaga
tgtctgtctc agcattgtct tccaagctcc taggccacag
tagtggggcg ctcccttctc tggcttcttc tttggtgaca
gtcaaggtgg ggttgggggt gacgaagggt cctgcttctc
ttctaggagc agttgatccc aggaagagca ttggagcctc
cagcagggc tgttgggcc tgtctgagga gataggatgc
gtcaggcagc cccagacacg atcacattcc tctcaacatg
cctgccgggg tctgtggagc cgaggggctg atgggagggt
ggggtggggg ccggaagggt ttgctttggg aggttgtctg
ggagattgct gaagttttga tatacacacc tccaaagcag
gaccaagtgg actcctagaa atgtcccctg acccttgggg
cttcaggagt cagggaccct cgtgtccacc tcagccttgc
ccttgcacag cccagctcca ctccagcctc tactcctccc
cagaacatct cctgggccag ttccacaagg ggctcaaacg
agggcacctg agctgccac actaggatg ttctgggggt
ctgagaagat atctgggct ggaagaataa aaggccccc
taggcctgtt cctggatgca gctccagcca cttttgggct
aagcctgggc aataacaatg ccaacgaggc ttcttgccat
actcggttta caaaacccctt tacatacatt gtcgcattgg
attctcagag ctgactgcac taagcagaat agatggtatg
actcccactt tgcagatgag aacactgagg ctcagagaag
tgcgaagccc tgggtcacag aggcgtaaat gcagagcag
gacccacctg aagacccacc tgactccagg atgtttcctg
cctccatgag gccacctgcc ctatggtgtg gtggatgtga
gatcctcacc atagggagga gattagggtc tgtgctcagg
gctggggaga ggtgcctgga tttctctttg atggggatgt
tggggtggga atcacgatac acctgatcag ctgggtgtat
ttcagggatg gggcagactt ctcagcacag cacggcaggt
caggcctggg agggccccc agacctcctt gtctctaata
gagggtcatg gtgagggagg cctgtctgtg cccaaggtga
ccttgccatg ccggtgcttt ccagccgggt atccatcccc
tgcagcagca ggcttcctct acgtggatgt taaaggccca
ttcagttcat ggagagctag caggaaacta ggtttaaggt
gcagaggccc tgctctctgt caccctggct aagcccagtg
cgtgggttcc tgagggctgg gactccagg gtccgatggg
```

```
aaagtgtagc ctgcaggccc acacctcccc ctgtgaatca
cgcctggcgg gacaagaaag cccaaaacac tccaaacaat
gagtttccag taaaatatga cagacatgat gaggcggatg
agaggaggga cctgcctggg agttggcgct agcctgtggg
tgatgaaagc caaggggaat ggaaagtgcc agacccgccc
cctacccatg agtataaagc actcgcatcc ctttgcaatt
tacccgagca ccttctcttc actcagccctt ctgctcgctc
gctcacctcc ctcctctgca ccatgactac ctgcagccgc
cagttcacct cctccagctc catgaagggc tctgcggcat
cggggcggc atcggggcg ctccagccg catctcctcc
gtcctggccg agggtcctg ccgcgccccc agcacctacg
ggggcggcct gtctgtctca tcctcccgct tctcctctgg
gggagcctac gggctggggg gcggctatgg cggtggcttc
agcagcagca gcagcagctt tggtagtggc tttggggag
gatatggtgg tggccttggt gctggcttgg gtggtggctt
tggtggtggc tttgctggtg gtgatgggct tctggtgggc
agtgagaagg tgaccatgca gaacctcaGt gaccgcctgg
cctcctacct ggacaaggtc cgtgctctgg aggaggccaa
cgccgacctg gaagtgaaga tccgtgactg gtaccagagg
cagcggcctg ctgagatcaa agactacagt ccctacttca
agaccattga ggacctgagg aacaagattc tcacagccac
agtggacaat gccaatgtcc ttctgcagat tgacaatgcc
cgtctggccg cggatgactt ccgcaccaag tatgagacag
agttgaacct gcgcatgagt gtggaagccg acatcaatgg
cctgcgcagg gtgctggacg aactgaccct ggccagagct
gacctggaga tgcagattga gagcctgaag gaggagctgg
cctacctgaa gaagaaccac gaggaggaga tgaatgccct
gagaggccag gtgggtggag atgtcaatgt ggagatggac
gctgcacctg gcgtggacct gagccgcatt ctgaacgaga
tgcgtgacca gtatgagaag atggcagaga gaaccgcaa
ggatgccgag gaatggttct tcaccaagac agaggagctg
aaccgcgagg tggccaccaa cagcgagctg gtgcagagcg
gcaagagcga gatctcggag ctccggcgca caatgcagaa
cctggagatt gagctgcagt cccagctcag catgaaagca
tccctggaga acagcctgga ggagaccaaa ggtcgctact
gcatgcagct ggcccagatc caggagatga ttggcagcgt
ggaggagcag ctggcccagc tccgctgcga gatggagcag
cagaaccagg agtacaagat cctgctggac gtgaagacgc
ggctggagca ggagatcgcc acctaccgcc gcctgctgga
gggcgaggac gcccacctct cctcctccca gttctcctct
```
ggatcgcagt catccagaga tgtgacctcc tccagccgcc aaatccgcac caaggtcatg gatgtgcacg atggcaaggt ggtgtccacc cacgagcagg tccttcgcac caagaactga ggctgcccag ccccgctcag gcctaggagg cccccgtgt ggacac

The invention claimed is:

1. A method of cell nuclear transfer comprising the steps of
   a. providing at least one pig oocyte having a zona pellucida that is partly, but not completely, removed,
   b. separating the pig oocyte into at least two parts obtaining at least one cytoplast,
   c. establishing a pig donor cell or pig cell nucleus having desired genetic properties,
   d. fusing at least one pig cytoplast with the pig donor cell or membrane surrounded cell nucleus, and
   e. obtaining a reconstructed pig embryo.

2. The method according to claim 1, wherein at least a part of the zona pellucida is partly removed enzymatically.

3. The method according to claim 1, wherein the pig oocyte is separated into at least three parts obtaining at least two cytoplasts.

4. The method according to claim 1, wherein the desired genetic properties of the pig donor cell or pig cell nucleus has been obtained by modifying the desired gene or genes by mutation, deletion and/or insertion.

5. The method according to claim 1, wherein the method of fusion is selected from the group consisting of chemical fusion, electro fusion and biofusion.

6. The method according to claim 1, wherein the fusion is performed in at least one step.

7. The method according to claim 1, wherein the fusion is performed in at least two steps.

8. The method according to claim 5, wherein a first step of fusion is between the at least one pig cytoplast and the pig donor cell or membrane surrounded cell nucleus.

9. The method according to claim 5, wherein a second step of fusion is between the at least one fused pair of claim 6 and at least one pig cytoplast.

10. The method according to claim 1, wherein the pig donor cell is a somatic cell.

11. The method according to claim 10, wherein the somatic cell is selected from the group consisting of epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells.

12. The method according to claim 10, wherein the somatic cells are obtained from the group consisting of skin cells, lung cells, pancreatic cells, liver cells, stomach cells, intestinal cells, cardiac cells, reproductive organ cells, bladder cells, kidney cells, urethral cells and other urinary organ cells.

13. The method according to claim 1, wherein the somatic cell is a fibroblast cell.

14. The method according to claim 1, wherein the pig donor cell originates from a germ line cell.

15. A method for producing a genetically modified or transgenic pig comprising:
   a. providing at least one pig oocyte having a zona pellucida that is partly, but not completely, removed,
   b. separating the pig oocyte into at least two parts obtaining a pig oocyte having a nucleus and at least one cytoplast,
   c. providing a pig donor cell or cell nucleus with desired genetic properties gained by genetic manipulation,
   d. fusing at least one cytoplast with the pig donor cell or membrane surrounded cell nucleus,
   e. obtaining a reconstructed pig embryo,
   f. activating to mitosis the reconstructed pig embryo to form a multi cell pig embryo;
   g. culturing said pig embryo; and
   h. transferring said cultured pig embryo to a host pig such that the pig embryo develops into a genetically modified pig fetus;
   whereby said host pig delivers a live-born piglet developed from said genetically modified pig fetus.

16. A method for producing a genetically engineered or transgenic pig comprising:
   a. providing at least one pig oocyte having a zona pellucida that is partly, but not completely, removed,
   b. separating the pig oocyte into at least three parts obtaining at least one cytoplast,
   c. providing a pig donor cell or pig cell nucleus having desired genetic properties,
   d. fusing at least one cytoplast with the pig donor cell or membrane surrounded cell nucleus,
   e. obtaining a reconstructed pig embryo,
   f. activating to mitosis the reconstructed pig embryo to form a multi cell pig embryo,
   g. culturing said pig embryo, and
   h. transferring said cultured pig embryo to a host pig such that the pig embryo develops into a genetically modified pig fetus,
   whereby said host pig delivers a live-born piglet developed from said genetically modified pig fetus.

17. The method according to claim 15, wherein the method for activation of the pig reconstructed embryo is selected from the group of methods consisting of electric pulse, chemically induced shock, increasing intracellular levels of divalent cations and reducing phosphorylation.

18. The method according to claim 15, wherein steps d) and f) are performed sequentially or simultaneously.

19. The method according to claim 15, wherein the pig embryo is cultured in vitro.

20. The method according to claim 19, wherein the pig embryo is cultured in sequential culture.

21. The method according to claim 15, wherein the pig embryo is cryopreserved prior to transfer to a pig host mammal.

22. The method according to claim 1, wherein the pig embryo is at a blastocyst stage.

23. A method for cloning a genetically modified pig comprising
   a. providing a pig embryo as obtained in claim 1, wherein the desired genetic properties of the pig donor cell or nucleus according to claim 1, step (c) are gained by genetic manipulation, and
   b. transferring said pig embryo to a host pig such that the embryo develops into a genetically modified fetus,
   whereby said host pig delivers a live-born piglet developed from said genetically modified fetus.

24. A genetically modified pig obtained by the method as defined in claim 23, having in its tissue cells mitochondria from at least three different sows.

25. A genetically modified pig embryo obtained by the method as defined in claim 1, having in its tissue cells mitochondria from at least four different sows.

26. A method of culturing a reconstructed pig embryo (embryo) comprising
   a. providing at least one pig oocyte having a zona pellucida, that is partly, but not completely, removed,
   b. separating the pig oocyte into at least two parts obtaining an oocyte having a nucleus and at least one cytoplast,
   c. providing a pig donor cell or cell nucleus having desired genetic properties,
   d. fusing at least one cytoplast with the pig donor cell or membrane surrounded cell nucleus,
   e. obtaining the reconstructed pig embryo,
   f. activating to mitosis the reconstructed pig embryo to form a multi cell pig embryo, and
   g. culturing the pig embryo of step f.

27. The method according to claim 26, wherein the pig embryo is cultured in sequential medium.

28. The method according to claim 1, wherein the pig oocyte is separated into at least three parts, obtaining at least two cytoplasts.

29. The method according to claim 21, wherein said embryo is cryopreserved by a process comprising a step of delipating the at least one pig oocyte.

30. The method according to claim 1 wherein the pig oocyte and the pig donor cell or cell nucleus are both from domestic pigs.

31. The method according to claim 15 wherein the pig oocotye and the pig donor cell or cell nucleus are both from domestic pigs and the host pig is a domestic pig.

32. The method according to claim 16 wherein the pig oocotye and the pig donor cell or cell nucleus are both from domestic pigs and the host pig is a domestic pig.

33. The method according to claim 26 wherein the pig oocyte and the pig donor cell or cell nucleus are both from domestic pigs.

34. The method of claim 29, wherein the delipated pig oocyte is separated into at least two parts, obtaining a pig oocyte having a nucleus and at least one cytoplast.

35. The method according to claim 29, wherein said pig embryo is cultured to blastocyst stage prior to vitrification.

* * * * *

UNITED STATES PATENT AND TRADEMARK OFFICE
CERTIFICATE OF CORRECTION

PATENT NO. : 8,513,486 B2  Page 1 of 1
APPLICATION NO. : 12/066169
DATED : August 20, 2013
INVENTOR(S) : Du et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 690 days.

Signed and Sealed this

Fifteenth Day of September, 2015

Michelle K. Lee
*Director of the United States Patent and Trademark Office*

SEQUENCE LISTING

<160> NUMBER OF SEQ ID NOS: 1

<210> SEQ ID NO 1
<211> LENGTH: 3806
<212> TYPE: DNA
<213> ORGANISM: Homo sapiens

<400> SEQUENCE: 1

| | | |
|---|---|---|
| aagcttatat tccatgctag ggttctggtg ttggtgcgtg gggttggggt gggactgcag | 60 |
| aagtgccttt taagattatg tgattgactg atctgtcatt ggttccctgc catctttatc | 120 |
| ttttggattc ccctcggagg aggggaggaa ggagtttctt ttgggttttta ttgaatcaaa | 180 |
| tgaaagggaa agtagaggtg ttcctatgga ggggaggaag gagtttcttt tgggttttat | 240 |
| tgaatcaaat gaaagggaaa gtagaggtgt tcctatgtcc cgggctccgg agcttctatt | 300 |
| cctgggccct gcataagaag gagacatggt ggtggtggtg gtgggtgggg gtggtggggc | 360 |
| acagaggaag ccgatgctgg gctctgcacc ccattcccgc tcccagatcc ctctggatat | 420 |
| agcacccccct ccagtgagca cagcctcccc ttgccccaca gccaacagca acatgcctcc | 480 |
| caacaaagca tctgtccctc agccaaaacc cctgttgcct ctctctgggg aaattgtagg | 540 |
| gctgggccag ggtgggggga ccattctctg cagggagatt aggagtgtct gtcaggggcg | 600 |
| ggtggagcgg ggtgggccc tggcttactc acatccttga gagtcctttg ctggcagatt | 660 |
| tggggagccc acagctcaga tgtctgtctc agcattgtct tccaagctcc taggccacag | 720 |
| tagtggggcg ctcccttctc tggcttcttc tttggtgaca gtcaaggtgg ggttggggt | 780 |
| gacgaagggt cctgcttctc ttctaggagc agttgatccc aggaagagca ttggagcctc | 840 |
| cagcaggggc tgttggggcc tgtctgagga gataggatgc gtcaggcagc cccagacacg | 900 |
| atcacattcc tctcaacatg cctgccgggg tctgtggagc cgaggggctg atgggagggt | 960 |
| ggggtggggg ccggaagggt ttgctttggg aggttgtctg ggagattgct gaagttttga | 1020 |
| tatacacacc tccaaagcag gaccaagtgg actcctagaa atgtcccctg acccttgggg | 1080 |
| cttcaggagt cagggaccct cgtgtccacc tcagccttgc ccttgcacag cccagctcca | 1140 |
| ctccagcctc tactcctccc cagaacatct cctgggccag ttcacaagg gctcaaacg | 1200 |
| agggcacctg agctgccac actagggatg ttctgggggt ctgagaagat atctggggct | 1260 |
| ggaagaataa aaggcccccc taggcctgtt cctggatgca gctccagcca ctttggggct | 1320 |
| aagcctgggc aataacaatg ccaacgaggc ttcttgccat actcggttta caaaacccctt | 1380 |
| tacatacatt gtcgcattgg attctcagag ctgactgcac taagcagaat agatggtatg | 1440 |
| actcccactt tgcagatgag aacactgagg ctcagagaag tgcgaagccc tgggtcacag | 1500 |
| aggcgtaaat gcagagccag gacccacctg aagacccacc tgactccagg atgtttcctg | 1560 |
| cctccatgag gccacctgcc ctatggtgtg gtggatgtga tcctcacc ataggagga | 1620 |
| gattagggtc tgtgctcagg gctggggaga ggtgcctgga tttctctttg atggggatgt | 1680 |
| tggggtggga atcacgatac acctgatcag ctgggtgtat tcagggatg gggcagactt | 1740 |

-continued

```
ctcagcacag cacggcaggt caggcctggg agggccccc agacctcctt gtctctaata    1800
gagggtcatg gtgagggagg cctgtctgtg cccaaggtga ccttgccatg ccggtgcttt    1860
ccagccgggt atccatcccc tgcagcagca ggcttcctct acgtggatgt taaaggccca    1920
ttcagttcat ggagagctag caggaaacta ggtttaaggt gcagaggccc tgctctctgt    1980
caccctggct aagcccagtg cgtgggttcc tgagggctgg gactcccagg gtccgatggg    2040
aaagtgtagc ctgcaggccc acacctcccc ctgtgaatca cgcctggcgg gacaagaaag    2100
cccaaaacac tccaaacaat gagtttccag taaaatatga cagacatgat gaggcggatg    2160
agaggaggga cctgcctggg agttggcgct agcctgtggg tgatgaaagc caaggggaat    2220
ggaaagtgcc agacccgccc cctacccatg agtataaagc actcgcatcc ctttgcaatt    2280
tacccgagca ccttctcttc actcagcctt ctgctcgctc gctcacctcc ctcctctgca    2340
ccatgactac ctgcagccgc cagttcacct cctccagctc catgaagggc tctgcggcat    2400
cggggcggc atcggggcg gctccagccg catctcctcc gtcctggccg gagggtcctg    2460
ccgcgccccc agcacctacg ggggcggcct gtctgtctca tcctcccgct tctcctctgg    2520
gggagcctac gggctggggg gcggctatgg cggtggcttc agcagcagca gcagcagctt    2580
tggtagtggc tttggggag gatatggtgg tggccttggt gctggcttgg gtggtggctt    2640
tggtggtggc tttgctggtg gtgatgggct tctggtgggc agtgagaagg tgaccatgca    2700
gaacctcagt gaccgcctgg cctcctacct ggacaaggtg cgtgctctgg aggaggccaa    2760
cgccgacctg gaagtgaaga tccgtgactg gtaccagagg cagcggcctg ctgagatcaa    2820
agactacagt ccctacttca agaccattga ggacctgagg aacaagattc tcacagccac    2880
agtggacaat gccaatgtcc ttctgcagat tgacaatgcc cgtctggccg cggatgactt    2940
ccgcaccaag tatgagacag agttgaacct gcgcatgagt gtggaagccg acatcaatgg    3000
cctgcgcagg gtgctggacg aactgaccct ggccagagct gacctggaga tgcagattga    3060
gagcctgaag gaggagctgg cctacctgaa gaagaaccac gaggaggaga tgaatgccct    3120
gagaggccag gtgggtggag atgtcaatgt ggagatggac gctgcacctg gcgtggacct    3180
gagccgcatt ctgaacgaga tgcgtgacca gtatgagaag atggcagaga gaaccgcaa    3240
ggatgccgag gaatggttct tcaccaagac agaggagctg aaccgcgagg tggccaccaa    3300
cagcgagctg gtgcagagcg gcaagagcga gatctcggag ctccggcgca ccatgcagaa    3360
cctggagatt gagctgcagt cccagctcag catgaaagca tccctggaga acagcctgga    3420
ggagaccaaa ggtcgctact gcatgcagct ggcccagatc caggagatga ttggcagcgt    3480
ggaggagcag ctggcccagc tccgctgcga gatggagcag cagaaccagg agtacaagat    3540
cctgctggac gtgaagacgc ggctggagca ggagatcgcc acctaccgcc gcctgctgga    3600
gggcgaggac gcccacctct cctcctccca gttctcctct ggatcgcagt catccagaga    3660
tgtgacctcc tccagccgcc aaatccgcac caaggtcatg gatgtgcacg atggcaaggt    3720
ggtgtccacc cacgagcagg tccttcgcac caagaactga ggctgcccag ccccgctcag    3780
gcctaggagg ccccccgtgt ggacac                                        3806
```